(12) United States Patent
Lourenco et al.

(10) Patent No.: US 11,866,395 B2
(45) Date of Patent: Jan. 9, 2024

(54) PRODUCTION OF PETROCHEMICAL FEEDSTOCKS AND PRODUCTS USING A FUEL CELL

(71) Applicants: 1304338 Alberta Ltd., Edmonton (CA); 1304342 Alberta Ltd., Edmonton (CA)

(72) Inventors: Jose Lourenco, Edmonton (CA); MacKenzie Millar, Edmonton (CA)

(73) Assignees: 1304338 Alberta Ltd., Edmonton (CA); 1304342 Alberta Ltd., Edmonton (CA)

( * ) Notice: Subject to any disclaimer, the term of this patent is extended or adjusted under 35 U.S.C. 154(b) by 561 days.

(21) Appl. No.: 16/979,086

(22) PCT Filed: Feb. 7, 2019

(86) PCT No.: PCT/CA2019/050159
§ 371 (c)(1),
(2) Date: Sep. 8, 2020

(87) PCT Pub. No.: WO2019/169475
PCT Pub. Date: Sep. 12, 2019

(65) Prior Publication Data
US 2020/0407298 A1    Dec. 31, 2020

(30) Foreign Application Priority Data

| Mar. 7, 2018 | (CA) | CA 2997634 |
| Apr. 25, 2018 | (CA) | CA 3002749 |
| Sep. 6, 2018 | (CA) | CA 3016645 |

(51) Int. Cl.
*H01M 8/04* (2016.01)
*C07C 29/48* (2006.01)
(Continued)

(52) U.S. Cl.
CPC ......... *C07C 29/48* (2013.01); *H01M 8/04014* (2013.01); *H01M 8/0625* (2013.01)

(58) Field of Classification Search
CPC .................. H01M 8/04014; H01M 8/0625
See application file for complete search history.

(56) References Cited

U.S. PATENT DOCUMENTS

| 2,446,925 A | 8/1948 | Hemminger |
| 2,495,613 A | 1/1950 | Tuttle |

(Continued)

FOREIGN PATENT DOCUMENTS

| CA | 1098852 A1 | 4/1981 |
| CA | 2691392 A1 | 2/2007 |

(Continued)

OTHER PUBLICATIONS

International Search Report dated Aug. 26, 2010, issued in International Application No. PCT/CA2010/000530, filed Apr. 7, 2010, 3 pages.

(Continued)

*Primary Examiner* — Olatunji A Godo
(74) *Attorney, Agent, or Firm* — CHRISTENSEN O'CONNOR JOHNSON KINDNESS PLLC

(57) ABSTRACT

A method of producing petrochemicals using a hydrocarbon fuel cell includes the steps of operating the fuel cell to produce electricity, thermal energy, and one or more exhaust stream, the one or more exhaust stream comprising at least a carbon-containing gas and water, reacting at least a portion of the exhaust stream with the reactant stream of natural gas to produce one or more petrochemical streams in a reactor, and heating one or more reactants using at least a portion of at least one of the electricity and the thermal energy.

15 Claims, 17 Drawing Sheets

(51) Int. Cl.
  *H01M 8/04014* (2016.01)
  *H01M 8/0612* (2016.01)

(56) References Cited

U.S. PATENT DOCUMENTS

| | | | |
|---|---|---|---|
| 4,094,767 | A | 6/1978 | Gifford |
| 4,187,672 | A | 2/1980 | Rasor |
| 4,213,826 | A | 7/1980 | Eddinger et al. |
| 4,265,736 | A | 5/1981 | Thayer |
| 4,306,961 | A | 12/1981 | Taciuk |
| 4,323,446 | A | 4/1982 | Chervenak et al. |
| 4,404,086 | A | 9/1983 | Oltrogge |
| 4,459,201 | A | 7/1984 | Eakman et al. |
| 4,561,966 | A | 12/1985 | Owen et al. |
| 5,014,785 | A | 5/1991 | Puri et al. |
| 5,084,362 | A | 1/1992 | Farooque |
| 5,085,274 | A | 2/1992 | Puri et al. |
| 5,093,579 | A | 3/1992 | Amemiya et al. |
| 5,133,406 | A | 7/1992 | Puri |
| 5,232,793 | A | 8/1993 | Miyauchi et al. |
| 5,332,036 | A | 7/1994 | Shirley et al. |
| 5,402,847 | A | 4/1995 | Wilson et al. |
| 5,422,195 | A | 6/1995 | Bernard |
| 5,536,488 | A | 7/1996 | Mansour et al. |
| 6,187,465 | B1 | 2/2001 | Galloway |
| 6,432,565 | B1 | 8/2002 | Haines |
| 7,459,226 | B2 | 12/2008 | Huijsmans |
| 7,550,063 | B2 | 6/2009 | Gawad |
| 7,753,972 | B2 | 7/2010 | Zubrin et al. |
| 7,946,346 | B2 | 5/2011 | Zornes |
| 8,088,528 | B2 | 1/2012 | Lourenco et al. |
| 8,349,504 | B1 * | 1/2013 | Radovich .............. C10J 3/721 429/426 |
| 8,585,891 | B2 | 11/2013 | Lourenco et al. |
| 8,616,294 | B2 | 12/2013 | Zubrin et al. |
| 9,077,005 | B2 | 7/2015 | Berlowitz et al. |
| 9,132,415 | B2 | 9/2015 | Lourenco et al. |
| 9,605,523 | B2 | 5/2017 | Zubrin et al. |
| 10,014,541 | B2 | 7/2018 | Jamal et al. |
| 10,787,891 | B2 | 9/2020 | Millar et al. |
| 10,968,725 | B2 | 4/2021 | Lourenco et al. |
| 2003/0022035 | A1 | 1/2003 | Galloway |
| 2004/0115492 | A1 | 6/2004 | Galloway |
| 2004/0229103 | A1 | 11/2004 | Jahnke et al. |
| 2005/0220695 | A1 | 10/2005 | Abatzoglou et al. |
| 2005/0271914 | A1 | 12/2005 | Farooque et al. |
| 2006/0159967 | A1 | 7/2006 | Huijsmans et al. |
| 2007/0099038 | A1 | 5/2007 | Galloway |
| 2008/0296018 | A1 | 12/2008 | Zubrin et al. |
| 2009/0155637 | A1 | 6/2009 | Cui et al. |
| 2010/0163226 | A1 | 7/2010 | Zornes |
| 2010/0261938 | A1 | 10/2010 | Olah et al. |
| 2011/0094940 | A1 | 4/2011 | Weisselberg |
| 2011/0163011 | A1 | 7/2011 | Yarbro |
| 2011/0206571 | A1 | 8/2011 | Skinner et al. |
| 2011/0207002 | A1 * | 8/2011 | Powell .............. C10J 3/463 429/410 |
| 2012/0215566 | A1 | 8/2012 | Lourenco et al. |
| 2012/0251898 | A1 | 10/2012 | Lehar et al. |
| 2013/0118735 | A1 | 5/2013 | Jamal et al. |
| 2014/0272617 | A1 | 9/2014 | Berlowitz et al. |
| 2014/0272638 | A1 | 9/2014 | Berlowitz et al. |
| 2014/0338901 | A1 | 11/2014 | Sites et al. |
| 2015/0188172 | A1 | 7/2015 | Yun et al. |
| 2015/0361833 | A1 | 12/2015 | Hinders et al. |
| 2016/0130513 | A1 | 5/2016 | Galloway |
| 2016/0351930 | A1 | 12/2016 | Jahnke et al. |

FOREIGN PATENT DOCUMENTS

| | | |
|---|---|---|
| CA | 2641747 A1 | 10/2008 |
| CA | 2 515 999 C | 12/2012 |
| CA | 2690836 C | 2/2016 |
| CA | 2920656 C | 3/2018 |
| CN | 101498229 A | 1/2008 |
| CN | 102937016 A | 2/2013 |
| GB | 977905 A | 12/1964 |
| GB | 2471862 A | 1/2011 |
| JP | 04034861 A | 2/1992 |
| JP | 2006104261 A | 4/2006 |
| JP | 20100158860 A | 1/2010 |
| JP | 2012233534 A | 11/2012 |
| JP | 2015-502639 A | 1/2015 |
| WO | 2005/001977 A1 | 1/2005 |
| WO | 2010058750 A1 | 5/2010 |
| WO | 2010/115283 A1 | 10/2010 |
| WO | 2011/081665 A1 | 7/2011 |
| WO | 2012/000115 A1 | 1/2012 |
| WO | 2012/092404 A1 | 7/2012 |
| WO | 2013/074875 A2 | 5/2013 |
| WO | 2014/138208 A1 | 9/2014 |
| WO | 2015/059507 A1 | 4/2015 |
| WO | 2015/106820 A1 | 7/2015 |
| WO | 2017059515 A1 | 4/2017 |
| WO | 2017059516 A1 | 4/2017 |
| WO | 2017096467 A1 | 6/2017 |
| WO | 2017/132773 A1 | 8/2017 |
| WO | 2017/189785 A1 | 11/2017 |
| WO | 2018044913 A1 | 3/2018 |

OTHER PUBLICATIONS

International Search Report dated Oct. 31, 2011, issued in International Application No. PCT/CA2011/050403, filed Jun. 30, 2011, 3 pages.
International Search Report and Written Opinion dated Feb. 24, 2014, issued in International Application No. PCT/CA2013/050955, filed Dec. 12, 2013, 7 pages.
International Search Report and Written Opinion dated Jun. 20, 2016, issued in International Application No. PCT/CA2015/051022, filed Oct. 8, 2015, 7 pages.
Jacobs Consultancy, "Evaluation of Integrating a Molten Carbonate Fuel Cell (MCFC) With a SADG Facility," prepared for Alberta Innovates—Energy and Environment Solutions, Jul. 2015, 77 pages.
International Search Report and Written Opinion dated Feb. 21, 2017, issued in International Application No. PCT/CA2016/051408, filed Dec. 1, 2016, 9 pages.
Hisato, A., "Upgrading of Heavy Crude Oil—Supercritical Water Cracking Technology," JOGMEC Techno Forum 2014, Nov. 26-27, 2014, 27 pages.
Hill, R., et al., "Application of Molten Carbonate Fuel Cell for CO2 Capture in Thermal In Situ Oil Sands Facilities," International Journal of Greenhouse Gas Control 41:276-284, 2015.
Hamelinck, C.N., et al., "Potential for CO2 Sequestration and Enhanced Coalbed Methane Production in the Netherlands," NOVEM Programme No. 234.1, Mar. 2001 (ISBN 90-5847-020-4), 105 pages.
International Search Report dated Apr. 18, 2019, issued in corresponding International Application No. PCT/CA2019/050159, filed Feb. 7, 2019, 9 pages.

* cited by examiner

PRODUCTION OF PETROCHEMICAL FEEDSTOCKS AND PRODUCTS USING A FUEL CELL

FIELD

This relates to a method that recovers and converts exhaust streams from a fuel cell to produce petrochemical feedstocks and products, which may be done at near zero GHG emissions.

BACKGROUND

The production of petrochemicals is well understood, and typically involves energy intensive catalytic processes. The major development in these processes is on catalyst research to improve operating conditions and increase production efficiencies. The awareness of climate change challenges industry to reduce GHG emissions and to develop technologies that converts carbon dioxide into products. Dry methane reforming technology is the most suitable technology for converting $CO_2$ into new products by reacting it with natural gas to generate a syngas mixture of CO and $H_2$. The obstacles for dry methane reforming include its potential for carbon formation due to the lower H/C ratio and via the Boudouard reaction, it also has a less favourable thermodynamics that makes it more difficult to achieve a high rate of conversion for the reactants. These obstacles can be alleviated by specially designed catalysts, optimizing the $CO_2$:$CH_4$ ratio and operating conditions. The challenges in dry methane processing have been the development of a catalyst that is resistant to coke fouling and a high quality supply of carbon dioxide at high temperatures. The National Research Labs of Canada (NRCAN) has developed a dry methane reforming catalyst that is resistant to coke fouling. EPI has developed a process to recover a high quality stream of carbon dioxide from a fuel cell anode exhaust stream and deliver it at high temperatures for the dry reforming of methane. Present dry methane reforming processes require carbon dioxide recovery units that are energy intensive processes in recovering and preparing carbon dioxide for dry methane reforming.

Another commonly produced petrochemical is methanol, which is a large volume commodity chemical. The production of methanol is well understood, and is generally considered an energy intensive, catalytic process. Industrial methanol is produced mainly by indirect liquefaction of natural gas. The indirect liquefaction process is done in two steps; reforming natural gas into synthesis gas followed by conversion into methanol. Both of these steps are catalytic processes, therefore research on catalysts to improve reactor operating conditions and production efficiencies are paramount. One major issue in research development is the curtailment of costs for producing synthesis gas from natural gas, which accounts for about 60% of the costs in the production of methanol. The three main routes to convert natural gas to syngas are steam reforming (SMR), partial oxidation (PDX) and auto thermal reforming (ATR). The most widely used technology to produce syngas for methanol synthesis is steam reforming. The overall methane steam reforming is highly endothermic, with the heat required by the process reaction generally being supplied by burning natural gas. In the partial oxidation process, natural gas is reacted with insufficient oxygen. This reaction is exothermic and is conducted at high temperatures, typically greater than 1200° C. Modern methanol plants use auto thermal reforming, which combines steam reforming with partial oxidation, where heat produced by the exothermic partial oxidation reaction is consumed by the endothermic steam reforming reaction. This process can be done in separate reactors or in a single reactor by adding water and oxygen. The drawback to this process is the large production of carbon dioxide, which may be sequestered or vented into the atmosphere. The production of carbon dioxide and the awareness of climate change challenges industry to minimize greenhouse emissions, minimize energy consumption and enhance syngas processes to produce methanol.

SUMMARY

The present method was developed with a view to recover thermal energy and fuel cell exhaust streams to produce petrochemical feedstocks. The process added benefit is the recovery and conversion of carbon dioxide, (a GHG emission gas) to produce valuable products.

According to an aspect, the presently described process allows carbon dioxide to be recovered and converted into value added products using a dry methane reforming process to convert a mixture of natural gas and carbon dioxide into a syngas product of carbon monoxide and hydrogen, which is a premium feedstock in the production of petrochemicals. The present system and method may also be used to produce a wide spectrum of other petrochemicals from two components, natural gas and atmospheric air, at near zero GHG emissions. Natural gas and atmospheric air may be used as inputs into a fuel cell, which produces energy and components in its exhaust streams that may then be used to produce petrochemicals efficiently and economically. Typically, there will be a natural gas fuel stream to the fuel cell, and a reactant stream to the downstream reaction to produce petrochemicals. In one aspect, a fuel cell anode carbon dioxide exhaust stream is cooled, separated, condensed, recovered, pumped, heated and mixed with natural gas for the catalytic process of dry reforming. The process thus allows for the recovery of a waste stream and its thermal energy to produce valuable reactants.

According to an aspect, there is provided a process that recovers exhaust streams and thermal energy from a fuel cell and provides electrical energy for the production of petrochemicals at near zero GHG emissions.

The process of generating power with a natural gas fuel cell differs from standard power generation plants that use natural gas. In a fuel cell, natural gas is consumed at the anode through an electrochemical reaction that produces electricity and a hot exhaust stream of gases, mainly water vapor and carbon dioxide, whereas in combustion based power generation plants, the exhaust stream is mainly nitrogen oxides, with water and carbon dioxide being minor components by mass and or volume in the combustion exhaust stream. The fuel cell anode exhaust stream is mainly carbon dioxide and water vapor, which combined is less than 75% of the exhaust mass flow rate of power generation combustion process. The concentrated fuel cell anode exhaust stream with its thermal energy is an ideal source to recover and convert carbon dioxide into value added products. The anode exhaust stream is a by-product of producing electricity with a fuel cell. The thermal energy of this anode exhaust gas stream is typically partially recovered in cogeneration processes to supply heat before the exhaust gas is released into the atmosphere.

The proposed system and method may be used recover the fuel cell exhaust streams thermal energy and its components for other uses.

According to another aspect, the process may include some or all of the following features:

Power generation by chemical reaction of natural gas in a fuel cell.

No or reduced GHG emissions released into the atmosphere, as the fuel cell anode exhaust stream and its thermal energy are recovered to produce water and carbon dioxide, where the exhaust stream may be further mixed with natural gas as a feedstock, such as for a tri-reforming methane (TRM) unit.

Production of water, the anode chemical reaction by stoichiometry produces 2.25 Kg of water per Kg of methane.

Production of carbon dioxide, the anode chemical reaction by stoichiometry produces 2.75 Kg of carbon dioxide per Kg of methane.

Recovering a fuel cell anode exhaust stream thermal energy to heat; carbon dioxide, water and natural gas.

Recovering a fuel cell cathode exhaust stream thermal energy to heat steam, natural gas and atmospheric air.

Recovery and efficient production of carbon dioxide, water and nitrogen.

Conversion of carbon dioxide through dry reforming or tri-reforming.

Conversion of water into hydrogen and oxygen through electrolysis.

Conversion of nitrogen into ammonia through catalytic processes.

A method where a fuel cell is both an energy provider (thermal and electrical) and a producer of highly concentrated streams of carbon dioxide, water and nitrogen for other petrochemical uses, such as to produce syngas, methanol, or other petrochemicals. The streams may be separated, or used directly in a mixed state as an exhaust stream.

A method to produce petrochemicals at zero or near zero GHG emissions. It will be understood that the actual GHG emissions will depend on the process as a whole, such as the composition of the exhaust streams, the products being produced, the reactions used to produce the products, and the efficiency and/or overall design of the equipment used.

According to a further aspect, the process may produce electricity for use and or export from a fuel cell and recovers the thermal energy and components of its exhaust streams for other uses. The fuel cell may be various types of fuel cell such as a molten carbonate, a solid oxide or phosphoric acid. The process for the production of dry reforming feedstock may comprise:

First, reducing the natural gas pressure supply to the tri reformer and fuel cell anode through an expander generator to produce electricity and a refrigerant natural gas stream.

Second, the refrigerant natural gas fuel stream enters a series of heat exchangers in a counter-current flow with the gaseous anode exhaust stream to cool and condense the exhaust water and carbon dioxide components.

Third, the natural gas supply stream gives up its generated coolth energy in a series of counter-current heat exchangers cooling and condensing the anode exhaust gaseous stream and simultaneously preheating the natural gas to the anode exhaust temperature.

Fourth, the now-heated natural gas supply stream enters the fuel cell anode where it is converted by steam reforming and electrochemical reactions into electricity and produces a high temperature anode exhaust gas stream that is mainly carbon dioxide and water.

Fifth, the high temperature anode exhaust gas stream is pre-cooled in the counter-current flow heat exchanger with the natural gas supply stream.

Sixth, the anode exhaust gas stream is further cooled in a counter-current flow heat exchanger by the recovered and pump-pressurized carbon dioxide stream.

Seventh, the condensed water fraction of the anode exhaust gas stream is separated in a gas/liquid separator and the separated anode exhaust gaseous carbon dioxide stream is routed for further cooling in a counter-current heat exchanger with the recovered liquid carbon dioxide stream.

Eighth, the anode exhaust gaseous carbon dioxide stream is further cooled in a counter-current heat exchanger with a cold carbon dioxide gaseous stream.

Ninth, the anode exhaust gaseous carbon dioxide stream is further cooled in a counter-current heat exchanger with the refrigerant natural gas supply stream to cool and condense a portion of the anode exhaust carbon dioxide and passed through a carbon dioxide separator.

Tenth, the recovered liquid carbon dioxide stream is pumped and pressurized and passed through a heat exchanger in a counter-current flow with the anode exhaust stream to its maximum temperature recovery.

Eleventh, the recovered water stream is pumped and pressurized and then passed through a heat exchanger in a counter-current flow with the anode exhaust stream.

Twelfth, the gaseous carbon dioxide stream from the carbon dioxide separator is mixed with fresh air and catalysed in a catalytic oxidizer to heat this oxidant stream up to fuel cell cathode temperature. The cathode consumes oxygen from the air and the carbon dioxide to produce a carbonate ion that is transferred through the fuel cell electrolyte layer to the anode to react with the anode hydrogen producing; water, carbon dioxide and electricity.

Thirteenth, a portion of the recovered water is routed to produce steam in a counter-current flow heat exchanger with the cathode exhaust gas stream, and the steam is supplied to a reformer at the anode.

Fourteenth, the high temperature cathode exhaust gas stream is pre-cooled in a counter-current flow heat exchanger by a natural gas stream flowing to the fuel cell anode.

Fifteenth, the cathode exhaust stream is further cooled in a counter-current flow heat exchanger by steam flowing to the fuel cell anode.

Sixteenth, the cathode exhaust stream is cooled further in a counter-current flow heat exchanger by atmospheric air supply flowing to the fuel cell cathode.

Seventeenth, using electricity generated by the fuel cell to power electric furnaces or devices to meet energy requirements of the petrochemical-production process.

Eighteenth, a fuel cell is operated to produce electricity, water and carbon dioxide. The fuel cell anode exhaust recovered carbon dioxide and water, thermal and electrical energy combined with additional natural gas produces methanol through a tri reforming methane process at near zero GHG emissions.

According to a further aspect, the process may produce electricity for use and or export from a fuel cell and recovers the thermal energy and components of its exhaust streams for other uses. The fuel cell may be various types of fuel cell such as a molten carbonate, a solid oxide or phosphoric acid. The process for the production of dry reforming feedstock may comprise:

First, reducing the natural gas pressure supply to the tri reformer and fuel cell anode through an expander generator, producing electricity and a refrigerant natural gas stream.

Second, pre-heating the refrigerant natural gas fuel supply to the tri reformer and fuel cell by heat exchange with streams in the TRM unit.

Third, introducing the heated natural gas supply stream to the fuel cell anode where it is converted by steam reforming and electrochemical reactions into electricity and a high temperature anode exhaust gas stream of mainly carbon dioxide and steam.

Fourth, routing a portion of the anode exhaust stream to the cathode where oxygen supplied from atmospheric air and the carbon dioxide in the anode exhaust stream react to produce a carbonate ion which is transferred through the fuel cell electrolyte layer to the anode to react with the anode hydrogen producing; steam, carbon dioxide and electricity.

Fifth, mixing the remaining high temperature anode exhaust gas stream with natural gas and heated to TRM unit process pressure and temperature.

Sixth, pre-cooling the high temperature cathode exhaust gas stream in a counter-current flow heat exchanger by natural gas stream to the fuel cell anode.

Seventh, cooling the cathode exhaust stream further in a counter-current flow heat exchanger by steam to the fuel cell anode.

Eighth, cooling the cathode exhaust stream further in a counter-current flow heat exchanger by atmospheric air supply to the fuel cell cathode.

Ninth, if required or preferred, using electricity generated by the fuel cell in electric furnaces or electric devices to meet thermal energy requirements of the TRM unit.

Tenth, operating the fuel cell to produce electricity, carbon dioxide and steam. The fuel cell anode exhaust stream will be made up of mainly carbon dioxide and steam, thermal and electrical energy combined with additional natural gas produces methanol in a TRM unit at near zero GHG emissions.

In one aspect, the process may use a high temperature anode exhaust stream from a fuel cell that is mainly carbon dioxide and steam with a large amount of thermal energy, which is mixed with natural gas as a feed source to a TRM unit to produce petrochemicals, such as methanol.

The natural gas may be used as a refrigerant to help condense and separate water and/or carbon dioxide from the anode exhaust stream prior to being used to produce petrochemicals. Various approaches are possible. For example, the natural gas may be expanded to make use of the Joules-Thompson effect in a J-T valve, a turbo expander, a generator, etc. The cooling capacity of the natural gas may be increased by pressurizing the stream of natural gas and then cooling the pressurized stream in an air cooled fan prior to being expanded, or by passing the natural gas through an external refrigeration plant. As a further possibility, natural gas may be supplied as liquid natural gas (LNG), which is at cryogenic temperatures. As the natural gas is used as a refrigerant, it is heated by the stream it is cooling, and may be heated toward a target temperature that is required for the downstream reactions to produce petrochemicals.

As will hereinafter be described, the present method may operate at any site where natural gas is available, or may be made available. The recovered components of carbon dioxide, water and nitrogen may be converted into petrochemical feedstocks and or products. Typically, the recovered components will be recovered as a high temperature anode exhaust stream from a fuel cell in vapour form. If producing methanol, these components may then be mixed with natural gas and reacted in a TRM unit. The electricity produced in the fuel cell provides the motive and thermal energy requirements of petrochemical processes. This process provides for the production of petrochemicals at near zero GHG emissions.

As will hereinafter be further described, there is provided a method to produce petrochemical products and feedstocks from fuel cell exhaust streams, which includes a natural gas supply stream to a dry reformer and a fuel cell, first reducing the natural gas pressure through a gas expander/generator producing a refrigerant natural gas stream and electricity. The refrigerant natural gas stream is pre-heated in a series of counter-current heat exchangers to cool and condense carbon dioxide and water from a fuel cell anode exhaust stream. The heated fuel cell natural gas stream is further heated and fed to the fuel cell anode where first it is steam reformed to produce hydrogen and carbon dioxide, the hydrogen is further reacted with a carbonate ion to produce water, carbon dioxide and electricity. The anode hot exhaust gas stream, is cooled, condensed, separated, recovered, pressurized and heated for other process uses. The cathode exhaust stream of mainly nitrogen, is cooled, separated and recovered for other uses. The objective of the inventive process is to recover and convert the fuel cell exhaust stream components into products at near zero GHG emissions. In one example, the process may be used to produce natural gas using a high temperature anode exhaust stream of primarily carbon dioxide and steam; the natural gas stream may be pre-heated by process streams in a TRM unit; and high temperature anode exhaust gas stream may be mixed with natural gas and conditioned to the TRM unit at optimum operating pressure and temperature conditions to produce methanol.

According to an aspect, there is provided a method of producing petrochemicals using a hydrocarbon fuel cell, comprising the steps of operating the fuel cell to produce electricity, thermal energy, and one or more exhaust stream, the one or more exhaust stream comprising at least a carbon-containing gas and water, reacting at least a portion of the exhaust stream with the reactant stream of natural gas to produce one or more petrochemical streams in a reactor, and heating one or more reactants using at least a portion of at least one of the electricity and the thermal energy.

According to other aspects, the carbon-containing gas and the water may be produced from an anode of the hydrocarbon fuel cell, the one or more exhaust streams may further comprise a nitrogen-containing gas produced from a cathode of the hydrocarbon fuel cell, at least a portion of the thermal energy may be carried by the one or more exhaust streams, the thermal energy may be used to preheat the reactant stream of natural gas, the one or more petrochemical streams may comprise one or more of a group consisting of: synthesis gas, methanol, ammonia, urea, polymers, prepolymers, hydrocarbon fuels, acetic acid, and glycol, the method may further comprise the step of separating the carbon-containing gas and the water into separate streams using heat exchangers and phase separators, the reactant stream of natural gas may comprises methane, ethane, propane, or combinations thereof, the reactant stream of natural gas and the at least a portion of the exhaust stream may be preconditioned in heat exchangers using the thermal energy of the energy stream, the method may further comprise the step of powering at least one of material handling equipment and heating equipment of the reactor, the fuel cell may be powered by a fuel stream of natural gas, and the reactant stream of natural gas may comprise a slipstream of the fuel stream of natural gas, substantially all of the carbon in the carbon-containing gas may be consumed in the reaction, and the reaction may comprise two or more reactions conducted in parallel or in series.

According to an aspect, there is provided a method of manufacturing petrochemicals from exhaust streams of a fuel cell by condensing, recovering, pumping and heating exhaust streams of carbon dioxide, water and nitrogen while producing electrical and thermal energy, the method comprising the steps of providing a fuel cell having an anode and a cathode, a series of fluid streams connected to the fuel cell, and a plurality of heat exchangers that heat and cool selected fluid streams, supplying natural gas to the fuel cell in a fuel stream and to a petrochemical unit in a reactant stream connected to a petrochemical production unit, heating the fuel stream of natural gas in one or more second heat exchangers and mixing the heated fuel stream with steam at an anode of the fuel cell, pre-heating an air stream to meet a temperature requirement of a cathode of the fuel cell, cooling and separating the anode exhaust stream to produce a stream of condensed steam, a stream of condensed carbon dioxide, and a remaining anode exhaust stream, the remaining anode exhaust stream comprising unreacted residuals and carbon dioxide, the remaining anode exhaust stream being mixed with the air stream prior to being communicated to the cathode of the fuel cell, pressurizing and heating the stream of condensed carbon dioxide to achieve an operating pressure and temperature of one or more petrochemical production units, pressurizing and heating a first portion of the stream of condensed steam to produce the steam that is mixed with the heated fuel stream at the anode of the fuel cell, and pressurizing and heating a second portion of the stream of condensed steam to petrochemical units operating pressures and temperatures of one or more petrochemical production units According to other aspects, the remaining anode exhaust stream may be compressed to meet desired operations properties for the fuel cell, the method may further comprise the step of cooling the pressurized natural gas produce a refrigerant stream of natural gas that is used to cool the anode exhaust stream by passing the pressurized natural gas through a gas expander/generator to produce electricity or through a Joules-Thompson valve, the natural gas supply may comprise liquid natural gas (LNG), the method may further comprise the step of adding an external source of one or more of carbon dioxide, water and nitrogen to one or more petrochemical production units, the natural gas may be diverted from an existing gas processing plant or straddle gas plant, and the electricity generated in the fuel cell may supply motive power and thermal power to the one or more petrochemical production units.

According to an aspect, there is provided a tri-reforming methane (TRM) process, which is a method of direct methane to methanol conversion by mixing natural gas, carbon dioxide and water, that provides an alternative method for direct production of synthesis gas with desirable $H_2/CO$ ratios by reforming methane or natural gas using recovered and conditioned exhaust streams from a fuel cell. This TRM process may be used to deliver high purity streams of carbon dioxide and water at desirable pressures and temperatures from a fuel cell to meet the optimum conditions for tri-reforming with methane or natural gas. Moreover, additional motive and thermal energy for the process may be provided by electricity produced from the fuel cell, thus enabling the production of methanol at or near zero GHG emissions. These process described herein may be used to help recover and convert carbon dioxide into value added products, and therefore reducing the amount of carbon dioxide vented to atmosphere.

According to an aspect, the TRM process uses a fuel cell to provide both the reactants and energy to produce methanol at near zero GHG emissions. Moreover, the proposed process enables the production of methanol from natural gas and atmospheric air at near zero GHG emissions. A fuel cell may be beneficially used to produce energy and components from its exhaust streams to efficiently and economically produce methanol. In the disclosed process, a fuel cell anode exhaust stream that contains carbon dioxide and water is cooled, separated, recovered, pumped, heated and mixed with natural gas for the catalytic process of tri methane reforming.

As will hereinafter be further described, there is provided a method to produce methanol by mixing methane with recovered carbon dioxide and water from a fuel cell anode exhaust stream, which includes a supply of natural gas supply stream to a fuel cell and to a tri reformer reactor. According to an aspect, the method includes, first, routing two streams of natural gas; one to supply the fuel cell, and the other to supply the methane reformer. The natural gas pressure is reduced through gas expanders/generators to produce refrigerant natural gas streams and electricity. The refrigerant natural gas streams are pre-heated in a series of counter-current heat exchangers that also cool and condense carbon dioxide and water from a fuel cell anode exhaust stream. The heated fuel cell natural gas stream is further heated and fed to the fuel cell anode where it is steam reformed to produce hydrogen and carbon dioxide, and the hydrogen is further reacted with a carbonate ion in the fuel cell to produce water, carbon dioxide and electricity. The anode exhaust gas stream, which is hot, is, in sequence, cooled, condensed, separated, recovered, pressurized and heated for mixing and reacting with methane to produce methanol. The cathode exhaust stream of mainly nitrogen, is cooled and recovered for other uses or released into the atmosphere. The objective of the process is to recover and convert the fuel cell anode exhaust stream of carbon dioxide and water to mix and react with methane or natural gas to produce methanol.

According to an aspect, there is provided a method of producing petrochemicals using a hydrocarbon fuel cell, comprising the steps of operating the fuel cell to produce one or more exhaust stream, capturing at least one of the exhaust streams, mixing the captured exhaust streams with a stream of natural gas, and reacting the captured exhaust stream and the stream of natural gas to produce one or more petrochemical streams in a reactor.

According to other aspects, the exhaust stream may comprise at least a carbon-containing gas, at least water, or at least a nitrogen containing gas, at least a portion of the exhaust stream may be produced from an anode of the hydrocarbon fuel cell, the one or more petrochemical streams may comprise one or more of a group consisting of: synthesis gas, methanol ammonia, urea, polymers, prepolymers, hydrocarbon fuels, acetic acid, and glycol, the stream of natural gas may comprise methane, ethane, propane, or combinations thereof, and substantially all of the carbon in the carbon-containing gas may be consumed in the reaction.

According to an aspect, there is provided a method of producing methanol through the operation of a fuel cell, comprising the steps of providing a pressurized natural gas stream, diverting at least a portion of the pressurized natural gas stream as a natural gas fuel stream to a fuel cell and at least a portion as a reactant natural gas stream to a methanol production unit, expanding at least a portion of the pressurized natural gas stream to decrease the pressure of the pressurized natural gas stream to produce a refrigerant natural gas supply stream, operating the fuel cell to produce energy, an anode exhaust stream comprising carbon dioxide and water, and a cathode exhaust stream, passing the heated anode exhaust stream through a series of heat exchangers and separators to produce a stream of condensed water, a stream of condensed carbon dioxide, and a stream of gaseous carbon dioxide, heating the natural gas fuel stream for mixing with steam and reforming at a fuel cell anode, mixing an air stream with a portion of the carbon dioxide from the anode exhaust stream to form a fuel cell air supply, pre-heating the fuel cell air supply to meet an operating temperature of the fuel cell cathode, pressurizing and heating the stream of condensed carbon dioxide to a reactor operating pressure and temperature, pressurizing and heating a first portion of the stream of condensed water to produce steam for mixing with the heated natural gas fuel stream for the fuel cell anode reformer, and pressurizing and heating a second portion of the stream of condensed water to the reactor operating pressure and temperature.

According to other aspects, the anode exhaust stream may comprise unreacted residuals, the unreacted residuals being mixed with the air stream to form the fuel cell air supply, the unreacted residuals may be compressed to meet desired operations properties within a catalytic oxidizer, the at least a portion of the pressurized natural gas may be expanded using a Joules-Thompson valve or an expander/generator, at least a portion of the pressurized natural gas may be further pressurized to increase a cooling capacity of the natural gas supply stream, a refrigeration plant may be supplied to increase the refrigeration properties of the refrigerant natural gas supply stream, the pressurized natural gas stream may comprise liquid natural gas (LNG), an external source of carbon dioxide may be added to at least one of the stream of condensed carbon dioxide and the stream of gaseous carbon dioxide, an external source of treated water may be added to the stream of condensed water produced from the anode exhaust stream, the natural gas may be diverted from an existing gas processing plant or to a straddle gas plant, the energy generated by the fuel cell may supply motive power to the methanol production unit and surplus thermal power, substantially all of the carbon in the anode exhaust stream may be consumed, the fuel cell energy may be combined with the anode exhaust stream comprising carbon dioxide and water to generate methanol at the methanol production unit, and each of the reactant stream of natural gas, the stream of condensed carbon dioxide, and the stream of condensed water may be flow controlled and temperature controlled to meet optimum reaction operating conditions before and after mixing.

According to an aspect, there is provided a method of using a fuel cell anode exhaust stream consisting mainly of carbon dioxide and steam that is mixed with a supply of natural gas, the mixture being conditioned to an operating temperature and pressure sufficient to react in a TRM unit to produce methanol at near zero GHG emissions. The method comprises the steps of: providing a pressurized natural gas supply stream to a fuel cell and to a methanol production unit; providing a gas expander or expansion generator to produce electricity and a refrigerant natural gas supply stream as per the Joules Thompson effect while decreasing pressure of a gas stream; providing one or more cooling streams to the TRM unit; providing a jet pump or venturi driven by a pre-heated natural gas supply provided to a methanol unit that draws and mixes with the cathode exhaust stream; providing a pre-heated air stream for mixing with a re-circulated cathode exhaust stream to supply carbon dioxide to the fuel cell cathode for the production of carbonate ion; providing a fuel cell that generates power and is fueled by natural gas; providing an on-line electrical heater to achieve an operating temperature prior to feeding the mixture to the TRM unit.

In other aspects, the method may comprise one or more of the following features, alone or in combination: the generators/expanders may be employed to reduce natural gas pressure supply to the fuel cell and TRM unit; the jet pump or venturi may be employed to draw in the cathode exhaust stream and mix with natural gas supply to the TRM unit; Joules-Thompson valves may be employed in lieu of expanders/generators; the natural gas supply may be boosted to increase the pressure of the natural gas supply pressure to generators/expanders; the natural gas supply may be liquid natural gas (LNG) in lieu of a pressurized natural gas supply; an external source of carbon dioxide may be added to the TRM natural gas supply/cathode exhaust mixer; an external source of steam may be added to the TRM natural gas supply/cathode exhaust mixer; the proposed process may be located at any natural gas supply infrastructure or supplied with another source of natural gas, such as liquid natural gas; the electricity generated in the fuel cell may supply both motive power to the proposed TRM unit as well the process thermal power required such as electric furnaces and or electrical on-line heaters; the method may produce methanol at near zero GHG emissions by direct mixing of a stream from a fuel cell anode exhaust stream; a fuel cell anode exhaust stream of mainly carbon dioxide and steam may be directly mixed with a supply of natural gas to produce methanol; energy from the fuel cell, such as electrical and thermal, may be combined with co-products of carbon dioxide and steam to provide the means to meet proven and commercial methanol processes inputs to generate methanol at near zero GHG emissions; the reactant streams of natural gas and fuel cell anode exhaust may be controlled to pressure and temperature meet optimum reaction operating conditions in the TRM unit; a mixture of the reactant streams of natural gas with a fuel cell anode exhaust stream may be controlled to pressure and temperature optimum reaction operating conditions in catalytic or non-catalytic reactors units; a fuel cell anode exhaust stream may be employed as reactants in petrochemicals processes; a fuel cell cathode exhaust stream may be mixed with a supply of natural gas or other hydrocarbons gaseous streams such as ethane, propane, butane, etc. and conditioned to pressure and temperature to other catalytic or non-catalytic processes to produce other products.

In other aspects, the features described above may be combined together in any reasonable combination as will be recognized by those skilled in the art.

BRIEF DESCRIPTION OF THE DRAWINGS

These and other features will become more apparent from the following description in which reference is made to the appended drawings, the drawings are for the purpose of illustration only and are not intended to in any way limit the scope of the invention to the particular embodiment or embodiments shown, wherein.

DETAILED DESCRIPTION OF THE PREFERRED EMBODIMENT

The method will now be described with reference to FIG. 1 through 17.

As described herein, the method was developed with a view to recover and convert exhaust streams from a fuel cell into petrochemical feedstocks and products, preferably at near zero GHG emissions, although the actual emissions will depend on the process used in practice. The process uses a different approach to recover thermal energy from an exhaust stream to first condense its components and then use the same thermal energy to preheat and produce petrochemical feedstocks and products. The system here described separates, recovers and converts a fuel cell concentrated hot exhaust gas streams into petrochemical feedstocks and products at near zero GHG emissions. The system may also mix the hot exhaust stream with natural gas and condition the mixture to achieve pressures and temperatures at which a reaction may occur in a tri-reforming methane (TRM) unit.

As used herein, the term petrochemicals is intended to refer to products that are produced using a hydrocarbon as the input, in this case, natural gas. These products may be intermediate products, i.e., that are used to produce other products, or final products. This includes a wide range of petrochemical feedstocks or products that may be made using natural gas and the fuel cell exhaust streams as the reactants. The natural gas used as one of the reactants will generally be methane ($CH_4$), but other heavier hydrocarbons may also be used, such as ethane ($C_2H_6$), propane ($C_3H_8$), etc. The natural gas may be in various forms, such as rich natural gas, which is a mixture of methane and heavier hydrocarbons, liquid natural gas (LNG), pressurized liquid natural gas (PLNG), compressed natural gas (CNG), and the like.

The method and apparatus described herein may also take advantage of the thermal energy and electricity that is produced by the fuel cell to help fuel the petrochemical reaction. Examples of petrochemicals that may be produced include synthesis gas (or syngas), methanol, ammonia, urea, polymers, prepolymers, hydrocarbon fuels, acetic acid, glycol, etc., and examples of how these petrochemicals may be produced are described below. However, it will be understood that other types of petrochemicals may also be produced, using the various inputs described herein as reactants. In some circumstances, additional reactants may need to be supplied to supplement those available from the natural gas and from the fuel cell exhaust streams.

The present method may be used to convert the recovered exhaust streams of water, carbon dioxide and nitrogen into petrochemical feedstocks and products. This method recovers the exhaust gas streams of a fuel cell typically discharged into the atmosphere as a by-product of power generation to produce petrochemical feedstock and products at near zero GHG emissions. The applications of the methods described herein should, therefore, be considered examples.

Figure 1:
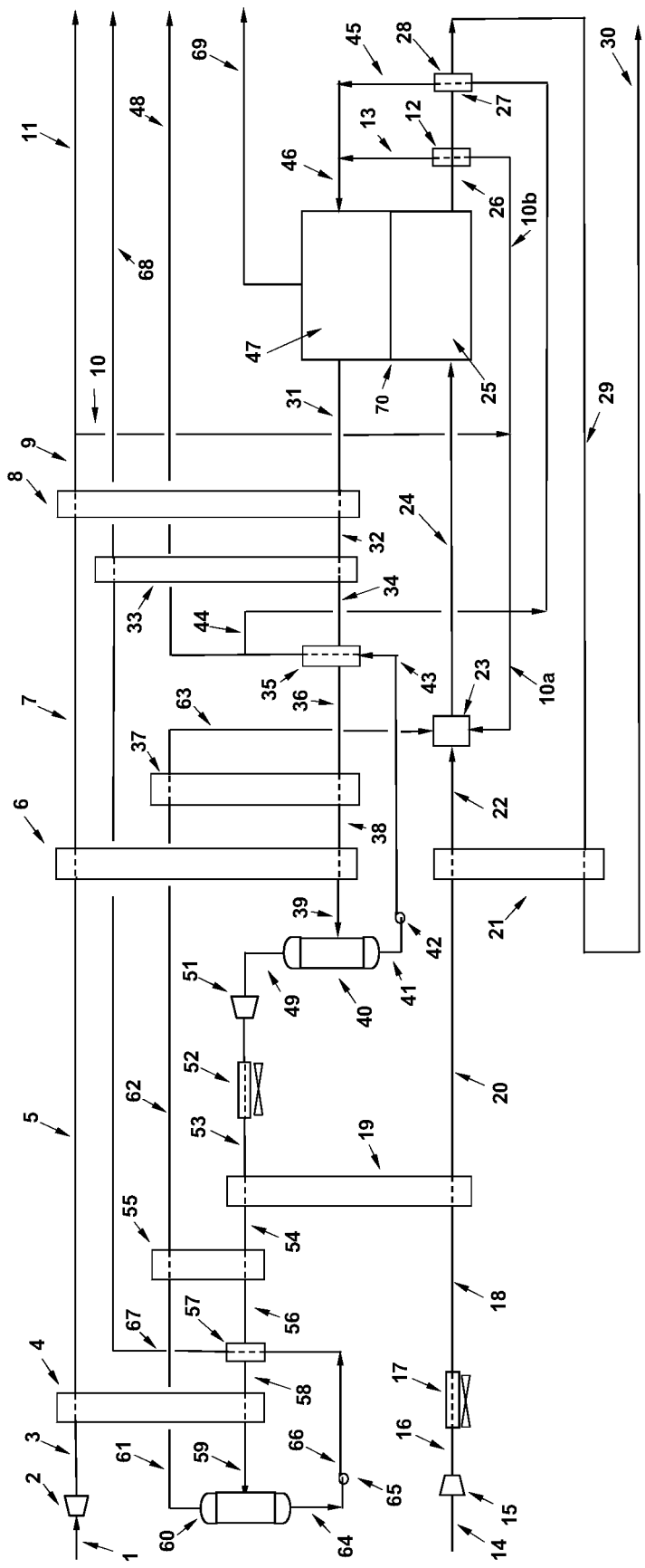
FIG. 1 is a schematic diagram of a preferred fuel cell exhaust stream recovery of its water, carbon dioxide, nitrogen and thermal energy for other uses such as carbon dioxide for the dry reforming of methane.

Referring to FIG. 1 an example of a method of recovering a fuel cell anode exhaust stream of water and carbon dioxide and its thermal energy to produce a carbon dioxide stream for dry reforming processes is shown. Fuel cells such as the Direct Fuel Cell (DFC) manufactured by Fuel Cell Energy in the USA have been available since 2003. The largest DFC power generation plant is a 59 MW built in South Korea. A major advantage of a DFC power generation plant versus standard power generation combustion process plants is the separated and highly concentrated mass flow rate of the exhaust gas streams allowing for ease of recovery and use relative to a combustion process.

Figure 3:
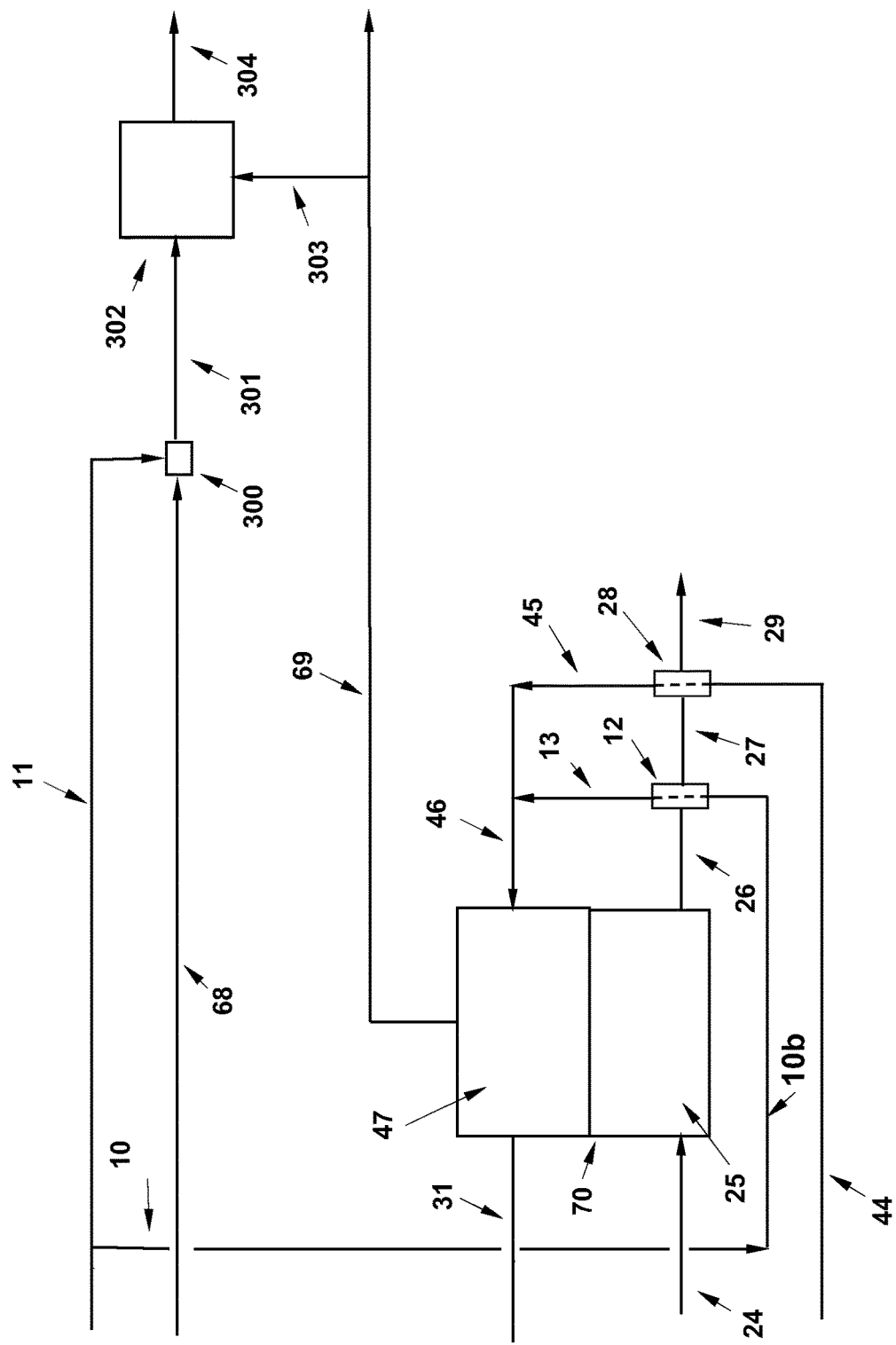
FIG. 3 is a schematic diagram of a method to produce a syngas of carbon monoxide and hydrogen by using a carbon dioxide stream produced in the fuel cell with natural gas.

Natural gas is delivered from a main transmission pipeline through stream 1 and enters an expander/generator 2 to reduce the main transmission pipeline pressure to meet fuel cell inlet pressure stream 3, during which the temperature of stream 3 is decreased from 1.5 to 2 degrees Celsius for every 15 psi pressure drop. The cooler natural gas stream 3 enters heat exchanger 4 to be heated by, and give up its coolth energy to, stream 58. The natural gas stream 5 is further heated in heat exchanger 6 by cooling stream 38. Natural gas stream 7 is further heated in heat exchanger 8 by cooling anode exhaust stream 31. The heated natural gas stream 9 is split into streams 10 and 11. The heated natural gas stream 11 is routed to other units, as shown in FIG. 3. A portion 10a of natural gas stream 10 may be routed to catalytic air pre-heater 23 to combust any unreacted hydrocarbons or hydrogen in stream 63. The remaining portion 10b of stream 10 is the natural gas feed to the fuel cell 70, and is further heated in heat exchanger 12 by fuel cell cathode exhaust stream 26. The heated fuel cell gas stream 13 is mixed with steam stream 45, and enters the fuel cell anode section 47, through stream 46. At fuel cell anode 47, the natural gas/steam stream 46 is first reformed to produce hydrogen and carbon dioxide, the hydrogen through an electrochemical reaction with a carbonate ion produced in cathode 25 and transferred through an electrolyte layer to the anode 47, produces electricity stream 69, and a hot anode exhaust stream 31. The carbonate ion produced in cathode 25 and transferred through an electrolyte layer into anode 47 is converted back to carbon dioxide in the electrochemical reaction. The main components of hot anode exhaust stream 31 are typically steam and carbon dioxide with some unreacted residuals of hydrogen and natural gas. The hot anode exhaust stream 31 enters heat exchanger 8 to give up some of its heat to natural gas stream 7, the cooler anode exhaust stream 32 is further cooled in heat exchanger 33 to give up more of its heat to carbon dioxide stream 67 to generate high temperature carbon dioxide stream 68. The cooler anode exhaust stream 34, is further cooled in heat exchanger 35 by water stream 43 to generate low pressure steam streams 44 and 48. The cooler anode exhaust stream 36, is further cooled in heat exchanger 37 by overhead carbon dioxide stream 62. The cooler anode exhaust stream 38, is further cooled in heat exchanger 6 by natural gas stream 5 and enters separator 40 to separate and collect the condensed water component of the anode exhaust stream 39. The concentrated carbon dioxide anode exhaust stream 49, exits separator 40 and pressurized by compressor 51, followed by air cooled fin/fan 52. The air cooled concentrated carbon dioxide stream 53 is further cooled in heat exchanger 19 by atmospheric air supply stream 18. Atmospheric air supply stream 18 is initially provided by stream 14, which is compressed by compressor 15 to produce compressed air stream 16, and then cooled in an air cooled fin/fan 17. The cooler concentrated carbon dioxide stream 54 is further cooled in heat exchanger 55 by concentrated carbon dioxide gaseous stream 67. The colder concentrated carbon dioxide anode exhaust 56 is further cooled in heat exchanger 57 by liquid carbon dioxide stream 66 and further cooled in heat exchanger 4 by expanded natural gas stream 3. The cold concentrated carbon dioxide anode exhaust stream 59 enters carbon dioxide separator 60 where the condensed carbon dioxide is separated from the gaseous fractions. The gaseous cold carbon dioxide stream and unreacted residuals stream 61 enters heat exchanger 55 to give up some of its coolth to anode exhaust stream 54, the warmer stream 62 is further heated in heat exchanger 37 by anode exhaust stream 36, the heated gaseous carbon dioxide and unreacted residuals stream 63 is mixed with air stream 22 at air pre-heater 23 where the unreacted residuals are catalytic oxidized and the oxidant stream 24 is heated to cathode 25 temperature. The fuel cell cathode 25 consumes the oxygen from the air and the circulated carbon dioxide from stream 63 to produce carbonate ion for transfer through an electrolyte to the fuel cell anode 47. The hot cathode exhaust stream exits fuel cell cathode 25 through stream 26, mainly nitrogen with residuals of carbon dioxide, water vapour and oxygen, enters heat exchanger 12 to heat fuel cell natural gas feed stream 10b, the heated natural gas stream 13 is mixed with steam stream 45, the mixed stream 46 is fed to the fuel cell anode 47 reformer to produce hydrogen and carbon dioxide. The cooled cathode exhaust stream 27 is further cooled in heat exchanger 28, heating fuel cell anode reformer steam supply stream 44 and the further cooled stream 29 is cooled in heat exchanger 21 by compressed and cooled atmospheric air supply 20 to air pre-heater 23. The cooled cathode exhaust stream 30 may be separated downstream to recover nitrogen for other uses.

The recovered water stream 41 from separator 40 enters pump 42 and is pumped into stream 43, routed to heat exchanger 35 and may be used to produce two steam streams 44 and 48. Steam stream 44 is recycled through heat exchanger 28 to the fuel cell anode 47 reformer. The other stream 48 of steam may be routed to other uses.

The recovered carbon dioxide liquid stream 64 from separator 60 is routed to pump 65 and pressurized for other process uses. The pressurized liquid carbon dioxide stream 67 is routed through heat exchanger 33 where it is heated by anode exhaust stream 32. The heated carbon dioxide stream 68 is routed for other process uses. The objective of the process is; first to recover and separate the components of a fuel cell exhaust streams by condensation in counter current heat exchange process configuration, second by pressurizing and heating the recovered liquids in a counter current heat exchange process configuration to produce streams for other uses. The innovation is in the recovery of components and thermal energy from a fuel cell exhaust streams of a fuel cell power generation plant and using these streams with power generated from the fuel cell 70 to produce petrochemicals at near zero GHG emissions.

Figure 2:
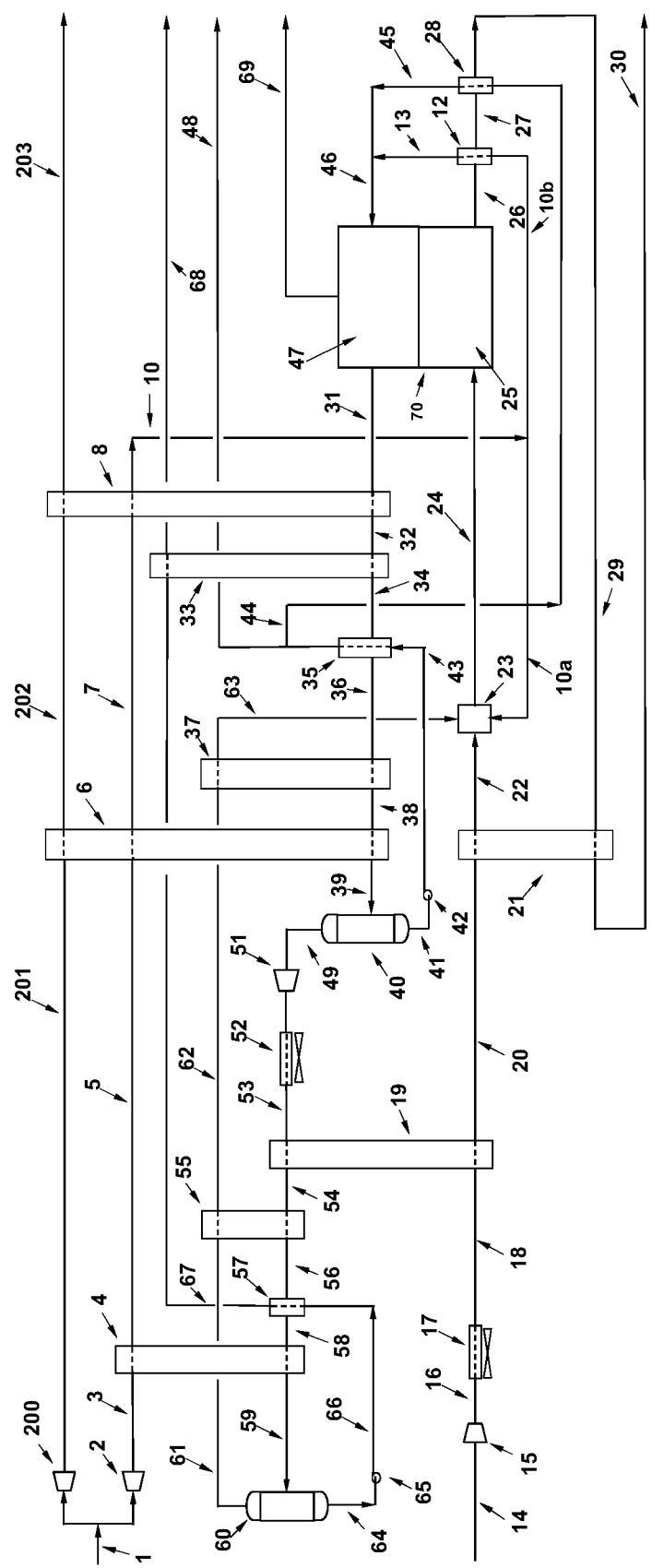
FIG. 2 is a schematic diagram of an alternative natural gas pressure expansion at two different operating pressures. One gas expander reduces the pressure to meet fuel cell pressure requirements while the other gas expander reduces the gas pressure to meet a catalytic reactor pressure requirements.

Referring to FIG. 2, another example is shown, which differs from FIG. 1 by routing a portion of natural gas stream 1 through a dedicated gas expander 200 which reduces the gas pressure to the pressure requirements for other uses other than as a fuel cell gas pressure supply. The different expanded gas pressure supply to other uses stream 201 is further heated in heat exchangers 6 to stream 202 and heat exchanger 8 to stream 203, which is routed for other process uses. In this example, natural gas stream 9 is not divided into two separate streams as is the case in FIG. 1, as stream 203 may be used for similar purposes as stream 11.

There will now be described different examples in which the products of the fuel cell 70 in FIGS. 1 and 2 are used to produce petrochemicals. Referring to FIG. 3, there is shown a process arrangement that may be used to produce syngas for petrochemical processes by the dry reforming process. The proposed method uses a carbon dioxide stream 68 which was condensed, separated, recovered, pressurized and heated from a fuel cell anode exhaust stream 31 (as shown in FIG. 1). A natural gas stream 11, preheated by fuel cell anode exhaust stream 31 (as shown in FIG. 1), is mixed with preheated carbon dioxide stream 68 in mixer 300. The mixed preheated mixture of carbon dioxide and natural gas stream 301 is routed to a dry catalytic dry reforming unit 302. The catalytic reaction in dry reforming is an endothermic reaction, electricity generated by the fuel cell 70 is delivered through electrical supply line 303 to dry reforming unit 302 to provide both thermal and motive energy. Some or all of the electricity 69 produced by the fuel cell 70 may be used to power an electric furnace or electric heating element devices to support and maintain an endothermic catalytic reaction, which may be used to enables the production of syngas at near zero GHG emissions in dry reforming unit 302. The produced syngas stream 304 of carbon monoxide and hydrogen can then be routed to other downstream catalytic processes such as acetic acid production, Fisher Tropsch processes, etc.

Those knowledgeable in the art will recognize and appreciate the many variations and use of this syngas produced by the proposed dry reforming, where both motive and electrical energy can be additionally supplied by a fuel cell 70 enabling these processes to produce petrochemicals at near zero GHG emissions.

Figure 4:
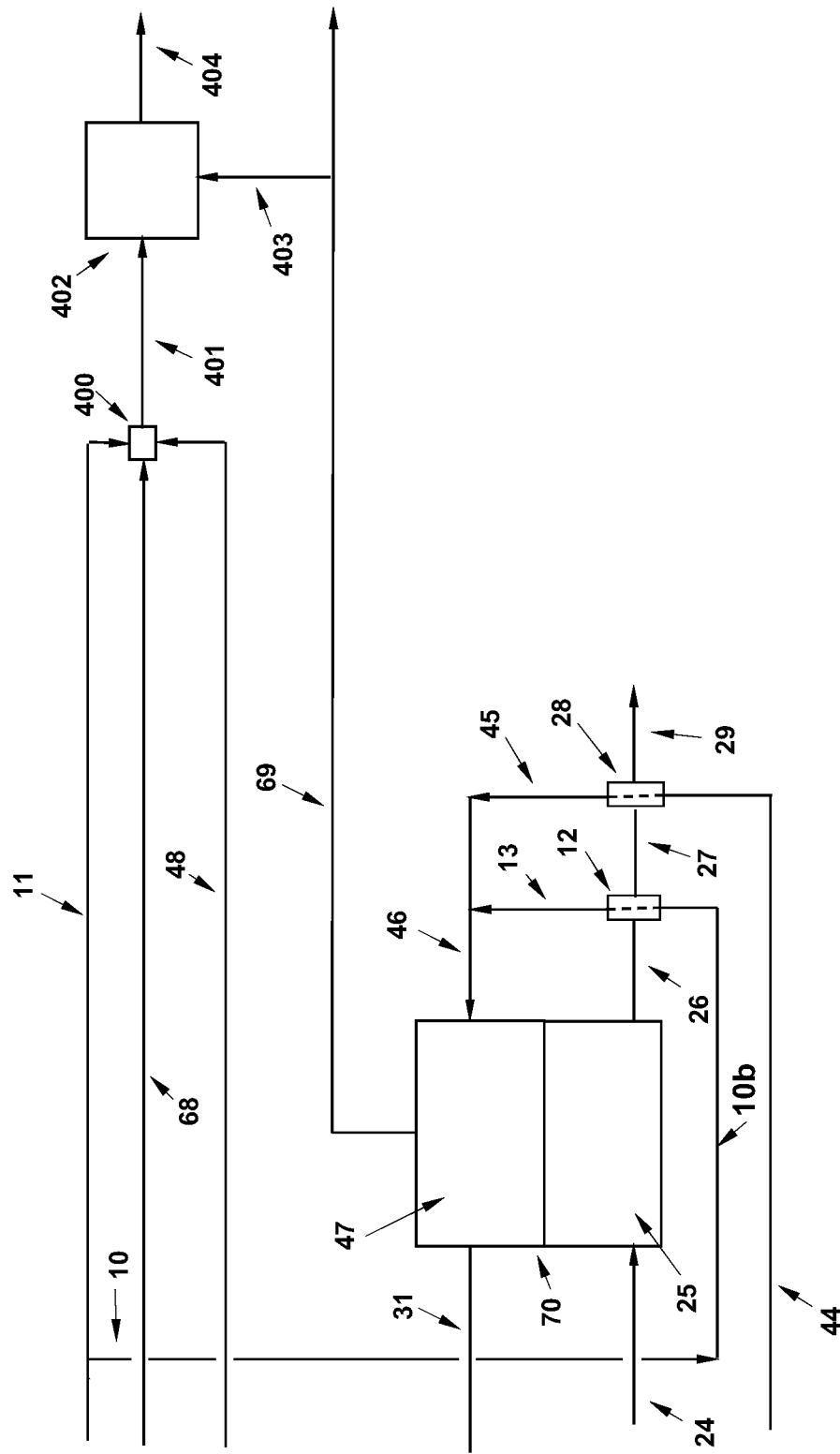
FIG. 4 is a schematic diagram of a method to produce methanol by using and combining streams of carbon dioxide and steam produced in the fuel cell with natural gas.

Referring to FIG. 4, another example of a process arrangement is shown, which differs from FIG. 3 in that it produces methanol by steam-carbon dioxide reforming of natural gas (methane). The proposed method uses a steam stream 68, which was produced by condensing, separating, recovering, pressurizing and heating it from a fuel cell anode exhaust stream 31 (as shown in FIG. 1). The steam stream 68 is added to mixer 400 along with preheated carbon dioxide stream 68 and preheated natural gas stream 11. The mixture stream of steam carbon dioxide and natural gas 401 is routed to methanol catalytic reactor unit 402, which produces methanol stream 404. The catalytic reaction in dry reforming is an endothermic reaction, electricity generated by the fuel cell 70 is delivered through electrical supply line 403 to methanol catalytic reactor unit 402 to provide both thermal and motive energy.

Those knowledgeable in the art will recognize and appreciate the feature of this method, where the reactants and energy produced by a fuel cell enables this process to produce methanol at near zero GHG emissions.

Figure 5:
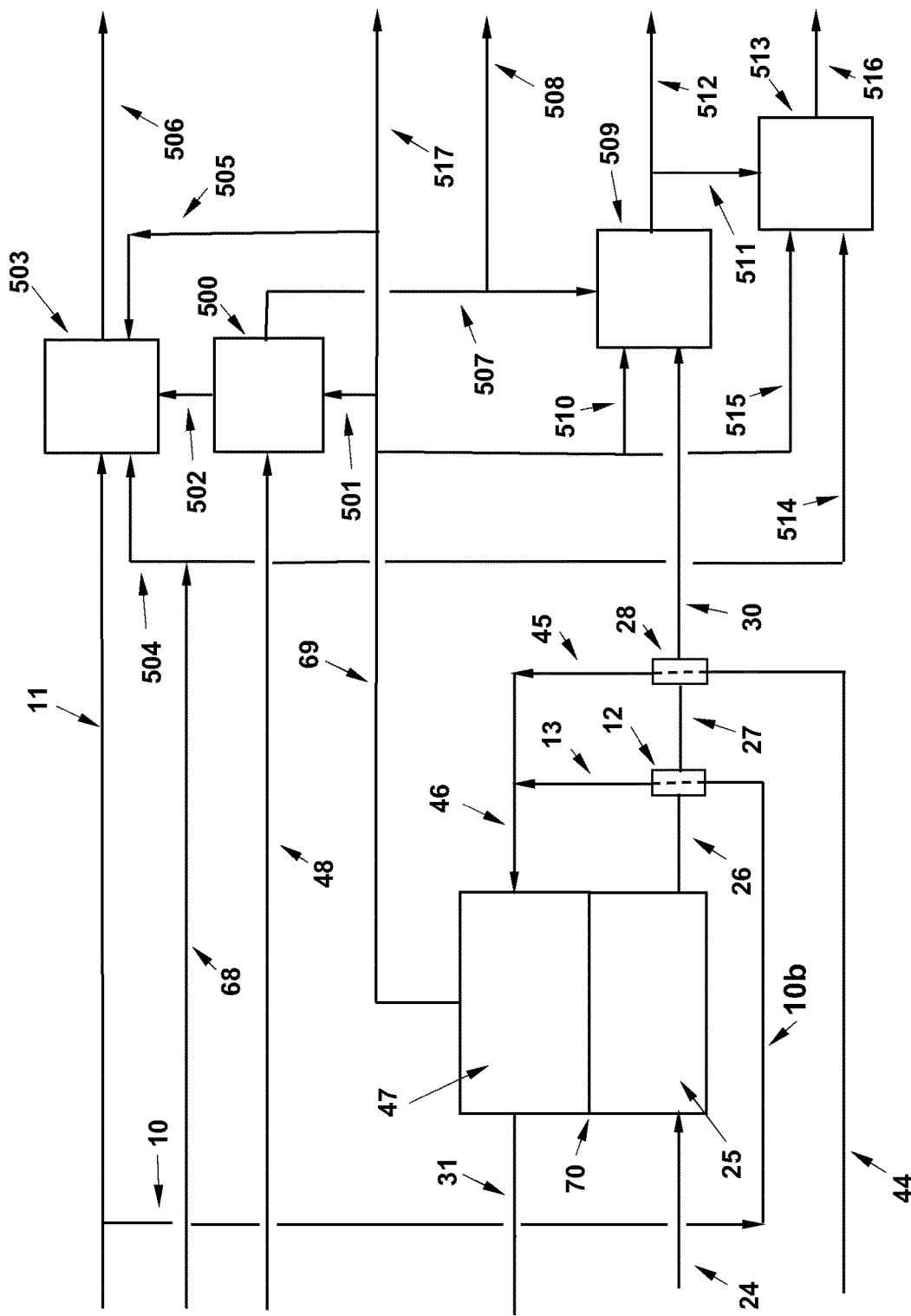
FIG. 5 is a schematic diagram of methods to produce various petrochemical feedstocks and products from streams of carbon dioxide, nitrogen and water produced at a fuel cell supported with electrical energy produced by the fuel cell to meet both motive and thermal energy process needs. Hence a fuel cell is both a provider of energy and reactants products.

Referring to FIG. 5, another example of a process arrangement is shown, in which a variation on the uses of recovered exhaust streams from the fuel cell 70 is designed to produce additional petrochemical products. The water and/or vapour stream 48 produced by the fuel cell 70 is routed to electrolyzer 500 to generate oxygen and hydrogen. The electricity requirements of electrolyzer 500 are supplied by electricity generated in the fuel cell power line 69 and routed to electrolyzer 500 through power line 501. The oxygen generated at electrolysis unit 500 routed through line 502 to auto thermal oxidation unit 503 to react with natural gas stream 11 and carbon dioxide stream 504 to produce syngas stream 506. The electrical energy requirements of the auto thermal oxidation unit 503 are supplied by fuel cell generated power line 69 through power line 505. The auto thermal reforming syngas product 506 may be routed to other catalytic units to produce petrochemicals and/or fuels. The hydrogen produced by electrolysis unit 500 may be routed through hydrogen stream 507 to an ammonia unit 509, and a portion may be diverted through line 508 for other uses. Nitrogen stream 30 produced and recovered from the fuel cell cathode stream 26 (as shown in FIG. 1) is routed to ammonia unit 509 for a catalytic reaction with hydrogen stream 507 to produce ammonia. The energy requirement of ammonia unit 509 is supplied through line 510. The ammonia stream 512 may be routed to storage or for other catalytic process through stream 511. The ammonia stream 511 may be routed to another catalytic unit 513, a urea unit. The carbon dioxide required for the production of urea may be supplied by fuel cell produced carbon dioxide stream 68, through line 514. The energy requirement for the production of urea is supplied by electricity generated by the fuel cell 70 through power line 515. The urea produced is routed to storage through line 516.

Those knowledgeable in the art will recognize and appreciate the feature of this method where the reactants and energy produced by a fuel cell enables various processes to produce petrochemical feedstock and products from two inputs natural gas and atmospheric air at near zero GHG emissions, in addition to the examples discussed above.

Fuel cells are presently in operation in sizes up to 59 MW and easily scalable to larger sizes. These power generation fuel cell sizes produce carbon dioxide, water and nitrogen streams as a byproduct of power generation that permits the production of petrochemicals at near zero GHG emissions using established and proven catalytic processes. In order to produce petrochemicals, these proposed processes use the highly concentrated, high quality streams of water, carbon dioxide and nitrogen. In addition, the thermal energy of the fuel cell exhaust streams is fully recovered to enhance the energy efficiency of these processes. Moreover, the use of produced electrical power to provide the thermal energy requirements of these catalytic processes through electric furnaces and or electric heating elements allows for the production of petrochemical products at near zero GHG emissions. As can be appreciated, the proposed methods provide many stream combinations to achieve desired petrochemicals feedstocks and or products. As an example, the auto thermal reformer can be operated with either a supply of carbon dioxide, methane and oxygen as shown, or with a supply of steam, methane and oxygen to achieve a different syngas ratio of $H_2:CO$ to meet a desired petrochemical feedstock or product. Additionally, the method also provides the means to reform higher molecular weight hydrocarbon fractions such as ethane, propane, etc., and/or dehydrogenation. The various combinations of mixing hydrocarbon streams with fuel cell derived energy (electrical+thermal) and carbon dioxide, nitrogen and water provide a method of producing petrochemical feedstocks and or products at near zero GHG emissions.

The proposed method also permits the efficient recovery of components and thermal energy from a fuel cell anode exhaust stream at a power generation plant to produce supercritical fluids.

Figure 6:
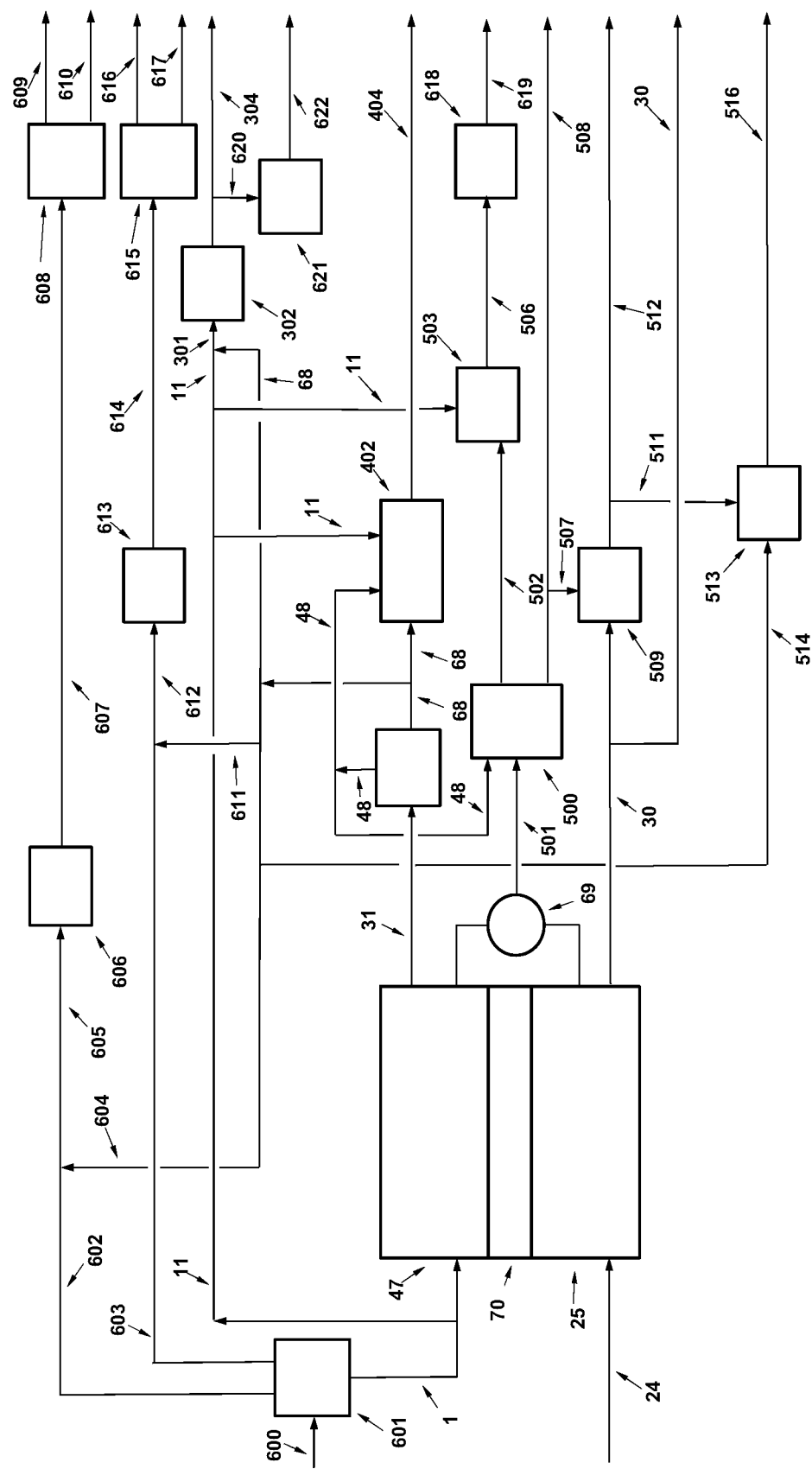
FIG. 6 is a schematic diagram of the methods to produce various petrochemical feedstocks and products from streams of carbon dioxide, nitrogen and water produced at a fuel cell supported with electrical energy produced by the fuel cell to meet both motive and thermal energy process needs. Hence a fuel cell is both a provider of energy and reactants products at near zero GHG emissions.

Referring to FIG. 6, there is shown a further example of the many possible methods that can be integrated with a fuel cell to produce petrochemical feedstocks and products two single inputs; natural gas and atmospheric air.

As indicated above on the many variations on integrating the fuel cell and its outputs with a natural gas stream, FIG. 6 depicts a process model where a rich natural gas stream is processed in unit 601 to produce a methane stream 1, an ethane stream 602 and a propane stream 603, it is understood although not shown that butane streams can also be produced in unit 601 and routed to other uses including syngas production or and fuels production. The gas processing unit 601 can be a gas processing unit, a gas straddle plant, or the like. The ethane stream 602 is mixed with carbon dioxide stream 604, the mixed stream 605 is routed to catalytic unit 606 for the catalytic dehydrogenation of ethane. The produced ethylene stream 607 is routed to petrochemical units shown as 608 that can be operated to produce various products such as polymers, stream 609 or chemicals such as ethylene glycol in stream 610.

The propane stream 603 is mixed with carbon dioxide stream 611, the mixed stream 612 is routed to catalytic unit 613 for the catalytic dehydrogenation of propane. The produced propylene stream 614 is routed to petrochemical units, shown as 615, that can be operated to produce various products such as polymers as stream 616 or fibres as stream 617.

A further example of the production of a petrochemical feedstock is the use of syngas stream 620 produced in the dry methane reformer unit 302 to feed a catalytic acetic acid unit 621 to produce acetic acid as stream 622. Moreover is the integration of syngas produced in the auto thermal reforming unit 503, through stream 506 to a Fisher Tropsch unit 618 to produce synthetic fuels stream 619.

Figure 7:
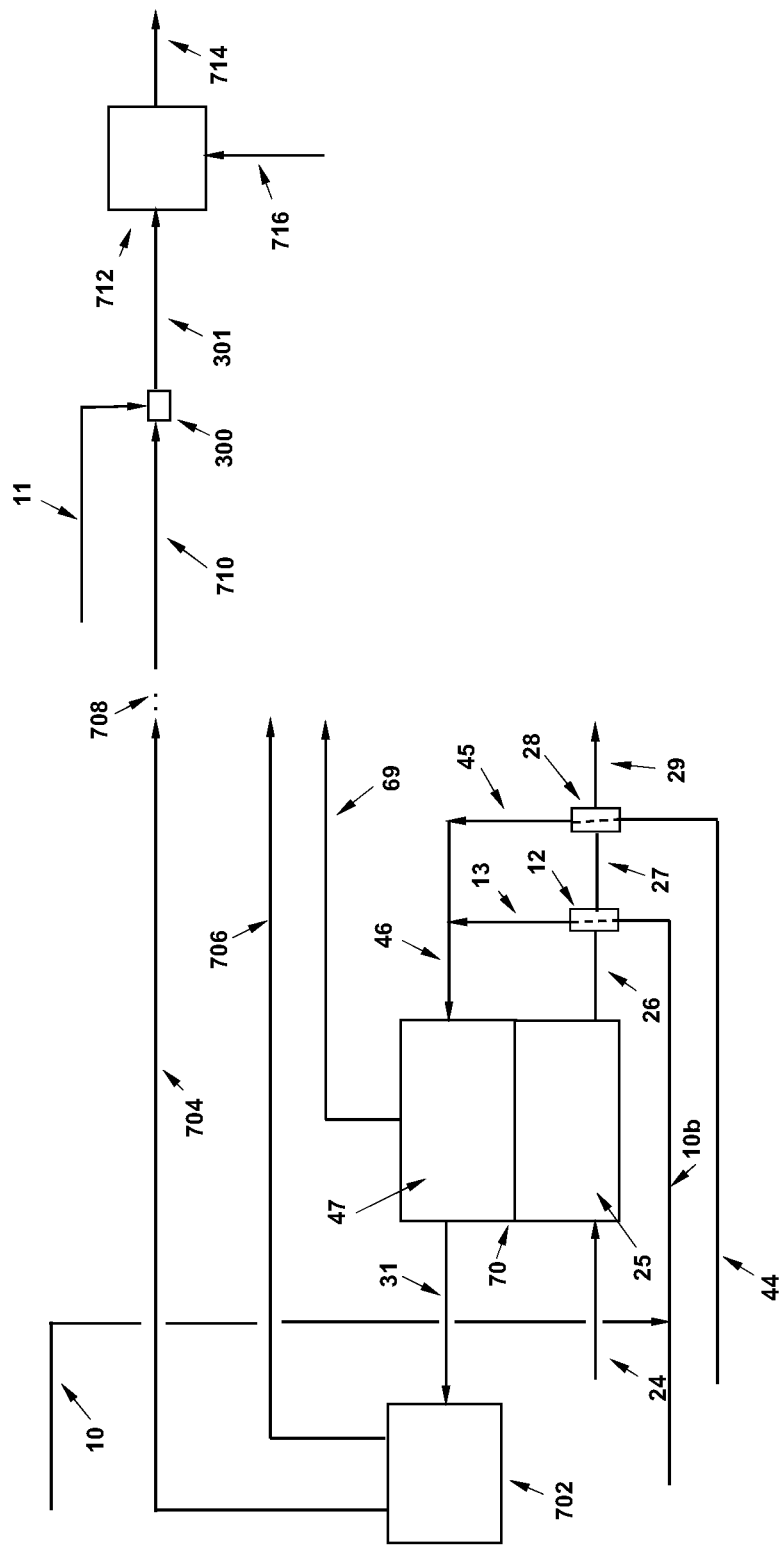
FIG. 7 is a schematic diagram of a method to produce petrochemicals using a carbon dioxide stream produced in the fuel cell with natural gas.

Referring to FIG. 7, a further example of a method of producing petrochemicals is shown. In this example, petrochemicals may be produced at a separate location using one or more exhaust products produced from the fuel cell.

In this example, a portion 10b of a natural gas stream 10 passes through a heat exchanger 12 and enters the fuel cell anode section 47 through stream 46. Other process such as those depicted using stream 44 and heat exchanger 28 may also be employed in processing inputs to fuel cell 70. Fuel cell 70 is operated to produce one or more exhaust streams, such as hot anode exhaust stream 31, which includes carbon dioxide and water, and hot cathode exhaust stream 26, which includes a nitrogen-containing gas. Fuel cell 70 also produces an electricity stream 69. As shown, hot anode exhaust stream 31 is separated in a processor 702 into stream 704 for carbon dioxide and stream 706 for the water. Processor 702 may take a number of forms as are known in the art, and examples of which are described herein. At least one of these exhaust streams 704, 706, 69, and 29 are captured for further processing. As shown, carbon dioxide stream 704 is captured for processing, however, it will be understood that other streams may also be captured and used in a variety of combinations. Carbon dioxide stream 704 may be stored or transported to a processing facility as shown at 708, and may not be processed on site. Carbon dioxide stream 704 may also be treated, such as by preheating or pressurizing. The captured exhaust stream is then provided through stream 710 to a mixer 300 where it is mixed with a stream of natural gas 11. The mixture of carbon dioxide and natural gas 301 is then provided to a reactor 712 in which one or more petrochemical streams 714 are produced. The reaction between carbon dioxide and natural gas may involve methods described herein, or other methods as are known in the art. Additional reactants or energy inputs may be provided to reactor 712 at 716. These additional reactants or energy may include the outputs from 706, 69, and 29, or may include inputs from other sources. It will be understood that water stream 706 and nitrogen-containing gas stream 29 may also be transported for use in reactor 712, or may be transported to other locations or for other purposes. It will be understood that the carbon dioxide produced by the fuel cell may contain other carbon-containing components, and the exact composition will depend on the operation of the fuel cell.

Figure 8:
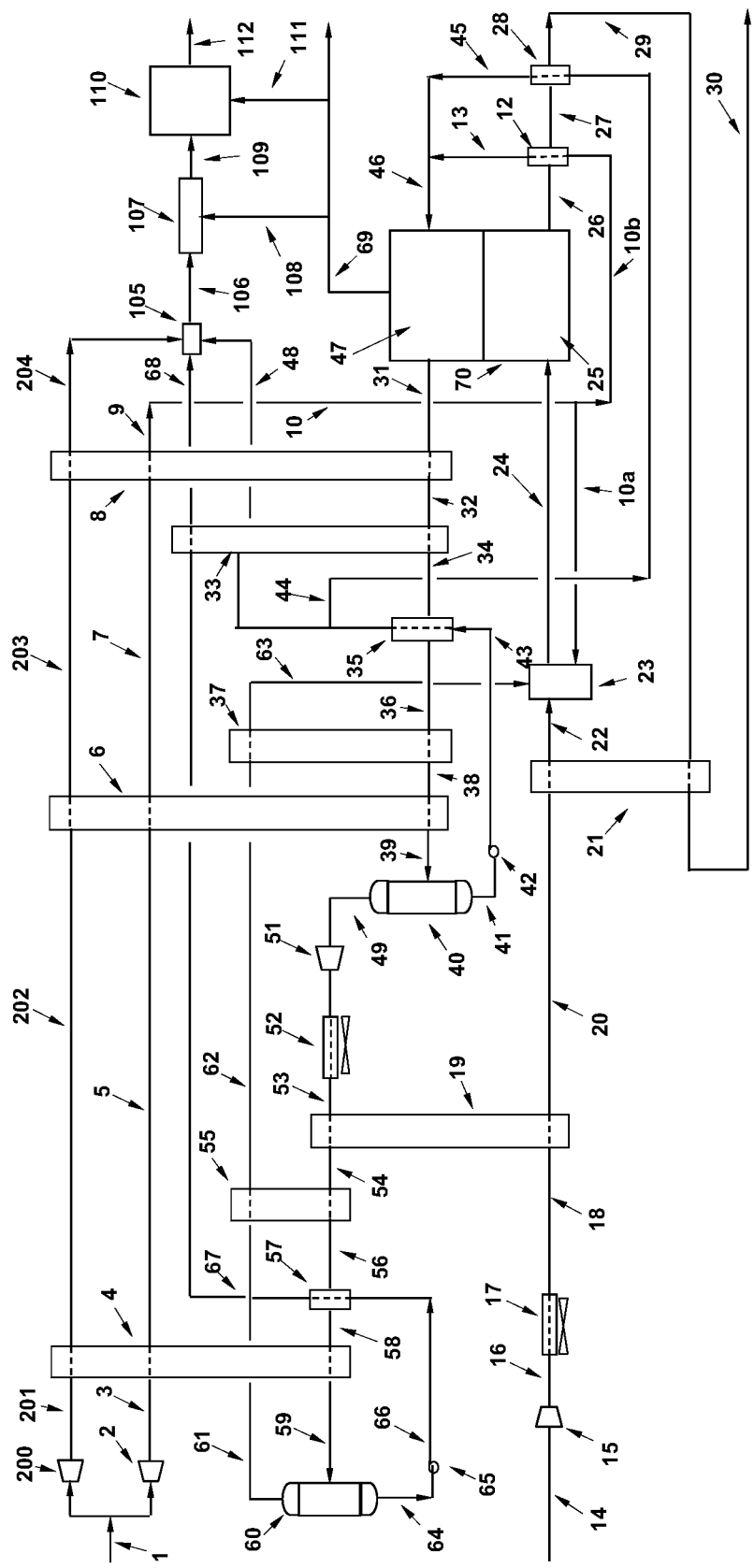
FIG. 8 is a schematic diagram of a fuel cell and tri reforming methane reactor process, showing the recovery of carbon dioxide, water and thermal energy from a fuel cell anode exhaust stream to mix and react with natural gas to produce methanol.

Referring to FIG. 8, there is shown a method of recovering a fuel cell anode exhaust stream of water and carbon dioxide and its thermal energy to mix and react with natural gas or methane to produce methanol in a direct methane to methanol tri reforming process. In the depicted example, natural gas and atmospheric air are shown as being delivered to fuel cell 70 and the recovered exhaust streams are separated and conditioned as described above.

Once obtained, the heated carbon dioxide stream 68 is then routed to a mixing chamber 105 to mix with preheated natural gas stream 204 and steam stream 48. A supply of natural gas stream 1 is routed through gas expander/generator 200 to supply a natural gas stream 201 to a tri reformer methane reactor 109. A refrigerant gas stream 201 is produced by expanding a high pressure natural gas stream 1 through gas expander 200. The expanded natural gas stream 201 is heated first in heat exchanger 4 by stream 58, the heated stream 202 followed by further heating in heat exchanger 6 by stream 38, the heated stream 203 is further heated in heat exchanger 8 by stream 31. The heated stream 204 enters mixing chamber 105 where it is mixed with heated carbon dioxide stream 68 and steam stream 48. The mixed stream 106 is heated to reaction temperature on an on-line electric heater 107 by electricity supplied through power line 108. The heated mixture of natural gas, carbon dioxide and steam is routed through line 109 to catalytic reactor 110 to produce a methanol stream 112. A power line 111 provides electricity to meet the energy requirements of unit 110. The objective of the process is first, to recover and separate the components of a fuel cell exhaust streams by condensation in counter current heat exchange process configuration; and second, by pressurizing and heating the recovered liquids in a counter current heat exchange process configuration to produce streams of carbon dioxide and water to mix and react with natural gas to produce methanol. The example described above discloses a process that is able to recover components and thermal energy from exhaust streams of a fuel cell power generation plant, and uses these streams by mixing them with natural gas and bringing these mixed and heated components to reaction temperature by using power generated from the fuel cell to produce methanol at near zero GHG emissions.

Figure 9:
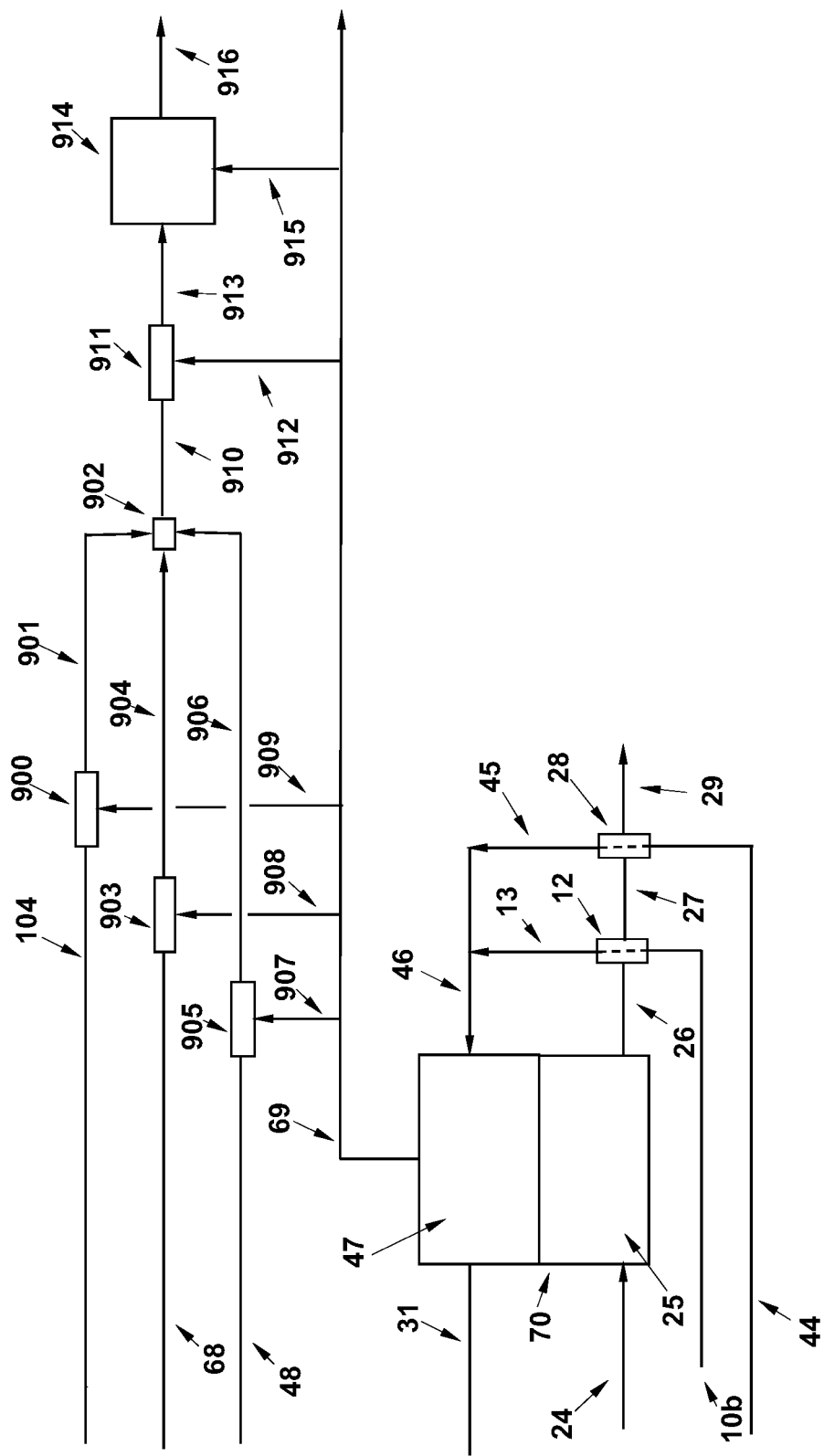
FIG. 9 is a variation of the process in FIG. 8, where the reactant streams temperature and flow ratios are individually controlled before mixing, followed by the temperature optimization of the mixture to reaction temperatures in a on-line electric heater.

Referring to FIG. 9, a modification of the process of FIG. 8 is shown. The process arrangement differs from FIG. 8 by being able to individually control each reactant flowrate and stream temperature to optimum operating conditions before mixing. After mixing, the optimum reaction temperature of the mixture is controlled by an on-line electric heater 911 before entering the reactor 914. The proposed method uses a steam stream 48 which was produced by condensing, separating, recovering, pressurizing and heating it from a fuel cell anode exhaust stream 31 (as shown in FIG. 8). The flow controlled preheated steam stream 48 is heated to optimum reactant temperature by an on-line electric heater 905. The electricity to heater 905 is supplied by power line 907. The flow controlled heated steam stream 906 enters mixing chamber 902. The flow controlled preheated carbon dioxide stream 68 is further heated to optimum temperature conditions in on-line electric heater 903. The electricity supply to heater 903 is provided by power line 908. The flow controlled heated carbon dioxide stream 904 enters mixing chamber 902. The flow controlled preheated natural gas stream 104 is heated to optimum reactant temperature by an on-line electric heater 900. The electricity to heater 900 is supplied by power line 909. The flow controlled heated steam stream 901 enters mixing chamber 902. The mixture of natural gas, carbon dioxide and steam exits mixing chamber 902 through line 910 and enters on-line electric heater 911 to heat the mixture to optimum reactor temperature operating conditions. The electricity to heater 911 is supplied by power line 912. The temperature controlled mixture stream 913 enters reactor 914 to produce methanol. The electricity required for reactor unit 914 operations is supplied by power line 915. The produced methanol stream exits reactor unit 914 for distillation and or storage.

To those knowledgeable in the art will recognize and appreciate the feature of this method were the reactants and energy produced by a fuel cell enables this processes to produce methanol at near zero GHG emissions.

To those knowledgeable in the art will recognize and appreciate the feature of this method were the reactants and energy produced by a fuel cell enables each reactant stream to be rationed and temperature controlled for optimum operating reactor conditions. The electrical energy supply produced in the fuel cell allows for methanol to be produced at near zero emissions. Moreover, those knowledgeable in the art will appreciate the efficiency of on-line electric heating versus the typical gas operated furnaces. The on-line electric heaters can also be an electric furnace. The ability to control the flow and temperature of each reactant before and after mixing the reactants allows for operations optimization to maximize the process efficiency.

Figure 10:
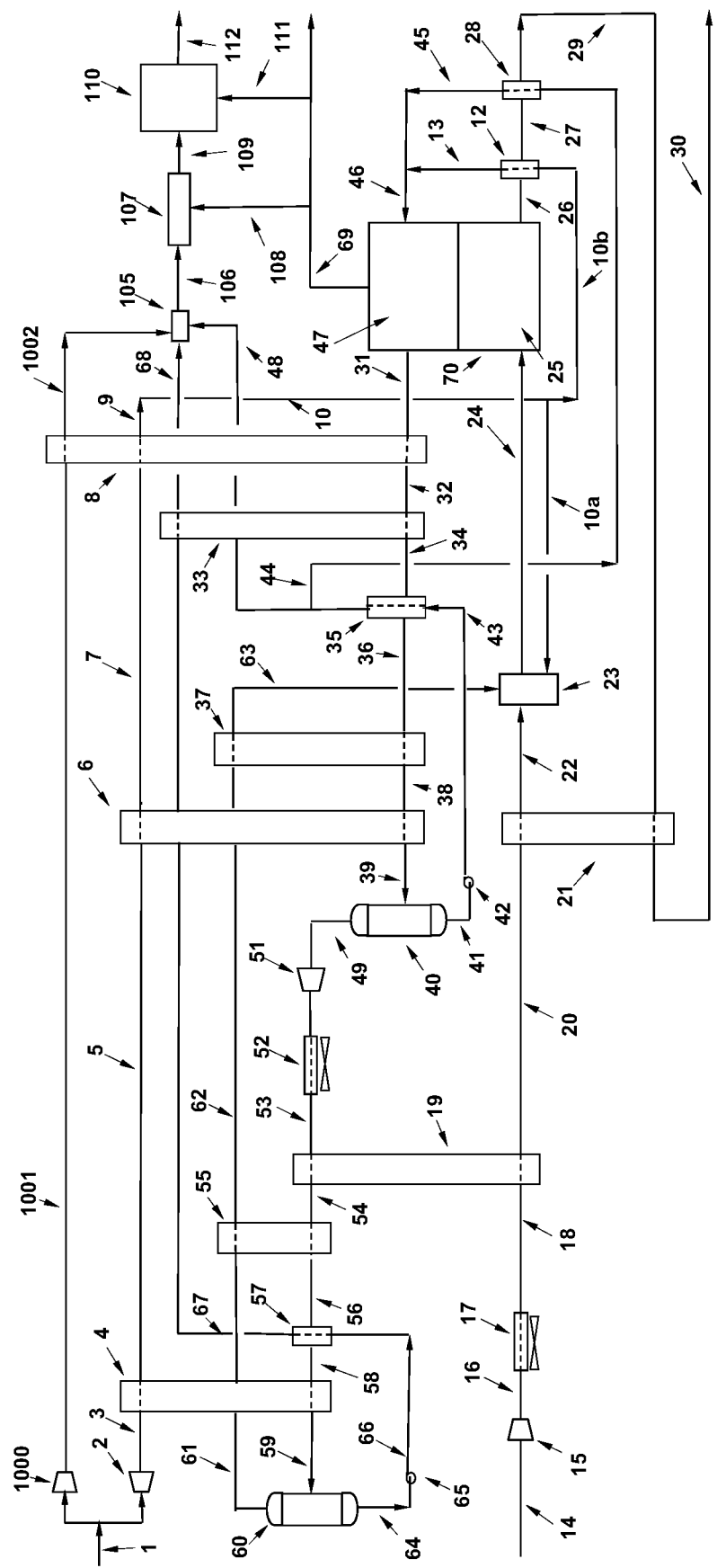
FIG. 10 is a variation of the process in FIG. 8, where a natural gas feed supply is compressed in order to meet the required conditions of a tri-reforming methane (TRM) reactor.

Referring to FIG. 10, another example is shown that differs from FIG. 8 by compressing the natural gas feed supply in a compressor 1000 if required to meet a TRM reactor operating at higher pressures. The higher pressure requirements for the carbon dioxide and water reactants are supplied by pumps 65 and 42 respectively. The proposed method uses a natural gas stream 1 entering compressor 1000 and pressurized to TRM operating pressure. The compressed natural gas stream 1001 is pre-heated in heat exchanger 8 by the anode exhaust stream 31. The preheated natural gas stream supply to the TRM 1002 enters mixing chamber 105 to mix with reactants carbon dioxide stream 68 and steam stream 48.

Figure 11:
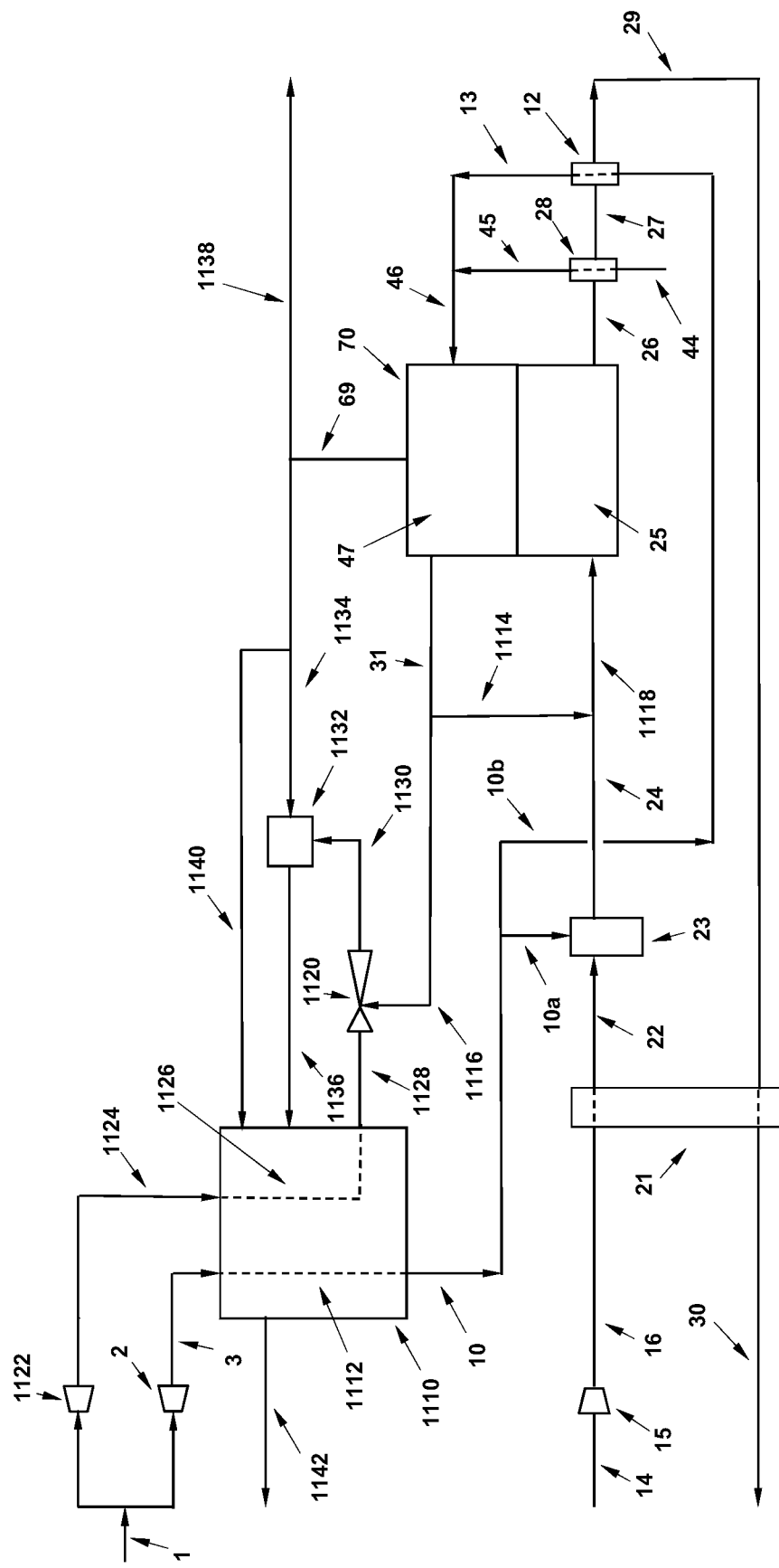
FIG. 11 is a schematic diagram of a fuel cell and TRM reactor process, showing a fuel cell anode exhaust stream mixing with natural gas, heated and reacted in a TRM unit to produce methanol.

Referring to FIG. 11 another configuration is shown in which a fuel cell anode exhaust stream of carbon dioxide and steam are mixed with natural gas or methane to produce methanol in a direct methane to methanol tri reforming process. Other possible design choices relative to the example in FIG. 11 are also depicted. One suitable type of fuel cell may include the Direct Fuel Cell (DFC) manufactured by Fuel Cell Energy in the USA, which have been available since 2003. One known DFC power generation plant is a 59 MW, built in South Korea. A major advantage of a DFC power generation plant versus standard power generation combustion process plants is the separated and highly concentrated mass flow rate of the exhaust gas streams allowing for ease of recovery and use versus a combustion process.

In this example, the components and thermal energy in an exhaust stream 31 from a fuel cell 70 that is used as a power generation plant are mixed with natural gas, and the mixture is conditioned to a required reaction temperature for a TRM unit by using power generated from the fuel cell. The TRM is then used to produce methanol at near zero GHG emissions.

Natural gas is delivered from main transmission pipeline through stream 1 and enters expander/generator 2, which reduces the pressure from the main transmission pipeline pressure to meet the pressure of fuel cell inlet pressure in stream 3. This also produces cold temperatures in stream 3, as the temperature of stream 3 is decreased from 1.5 to 2 degrees Celsius for every 15 psi pressure drop across gas expander 2. The cold natural gas stream 3 enters TRM unit 1110 to provide process cooling through stream 1112 in the TRM unit 1110. The natural gas stream 10 is split into two streams: stream 10a is a supply of natural gas that is provided to catalytic air heater 23, and stream 10b is a supply of natural gas that is supplied to fuel cell 70. Natural gas fuel cell supply stream 10b is heated in heat exchanger 12 by cathode exhaust stream 27. The heated fuel cell natural gas stream 13 is mixed with steam stream 45 to produce mixed stream 46, which enters anode section 47. At fuel cell anode 47, the natural gas/steam stream 46 is first reformed to produce hydrogen and carbon dioxide, where the hydrogen is produced through an electrochemical reaction with a carbonate ion produced in cathode 25 and transferred through an electrolyte layer to the anode 47, produces electricity in line 69, and a hot anode exhaust stream 31. The carbonate ion produced in cathode 25 and transferred through a fuel cell electrolyte layer into anode 47 is converted back to carbon dioxide in the electrochemical reaction. The main components in hot anode exhaust stream 31 are steam and carbon dioxide, with some unreacted residuals of hydrogen, carbon monoxide and natural gas. The hot anode exhaust stream 31 is split into streams 1114 and 1116. Stream 1114 is a recycling stream that supplies carbon dioxide to the cathode and mixes with stream 24. The mixed stream 1118 enters cathode section 25. The fuel cell cathode 25 consumes the oxygen from the air and the circulated carbon dioxide supplied by stream 1114 to produce a carbonate ion which is transferred through an electrolyte to the fuel cell anode 47. The hot cathode exhaust stream exits fuel cell cathode 25 through stream 26, made up mainly of nitrogen with residuals of carbon dioxide, water vapour and oxygen, enters heat exchanger 28 to heat steam stream 44. Steam stream 44 in this example may be from any suitable source of steam. The heated steam stream 45 is mixed with natural gas stream 13, and the mixed stream 46 is fed to the fuel cell anode 47 reformer to produce hydrogen and carbon dioxide. The pre-cooled cathode exhaust stream 27 is further cooled in heat exchanger 12 as it heats fuel cell anode reformer natural gas supply stream 10b. The cathode exhaust stream 29 is further cooled in heat exchanger 21 by atmospheric air supply stream 16 to air pre-heater 23. The cooled cathode exhaust stream 30 may be separated downstream to recover nitrogen for other uses. The air supply to the fuel cell cathode section 25 is provided by atmospheric air stream 14 through compressor 15 to reach the required operation pressure. The compressed air stream 16 is preheated in heat exchanger 21 and preheated, compressed air stream 22 is routed to catalytic burner 23 to meet the temperature requirements of fuel cell cathode 25. The heated air and flue gas stream mixes with anode exhaust recycling stream 1114 and enters the fuel cell cathode. The balance of anode exhaust stream 31, stream 1116 is routed to a jet pump 1120 to mix with natural gas and conditioned to react in the TRM unit.

A portion of natural gas stream 1 is routed through gas expander/generator 1122 to supply a natural gas stream 1124 to TRM unit 1110. The natural gas stream 1124 is cooled as it passes through expander 1122 and the pressure is reduced from the pressure in stream 1. The expanded natural gas stream 1124 provides process cooling to the TRM unit through stream 1126. The heated natural gas stream 1128 enters jet pump 1120 to provide the motive force to drawn in the cathode exhaust stream 1116, a mixture of mainly carbon dioxide and steam. The pressurized mixture of natural gas, carbon dioxide, steam and fuel cell residuals exits jet pump 1120 through stream 1130 into an on-line electric heater 1132, the heat is supplied by electrical line 1134, routed from line 69, to optimize the temperature of mixture stream 1136 to the TRM unit 1110 and produce methanol. The pressure for stream 1136 is controlled by the pressure letdown of expander/generator 1122 to arrive at an operating pressure for TRM unit 1110. An additional power line 1138 may be used to export excess power to other users, while power lines 1134 and 1140 deliver electricity to supply the power requirements of TRM unit 1110. As can be seen, the process mixes the fuel cell anode exhaust stream with natural gas and conditions the mixture to the required operating pressure and temperature conditions to react in a TRM unit 1110 to produce methanol. The produced methanol is then routed to through line 1142, for storage or transport.

Figure 12:
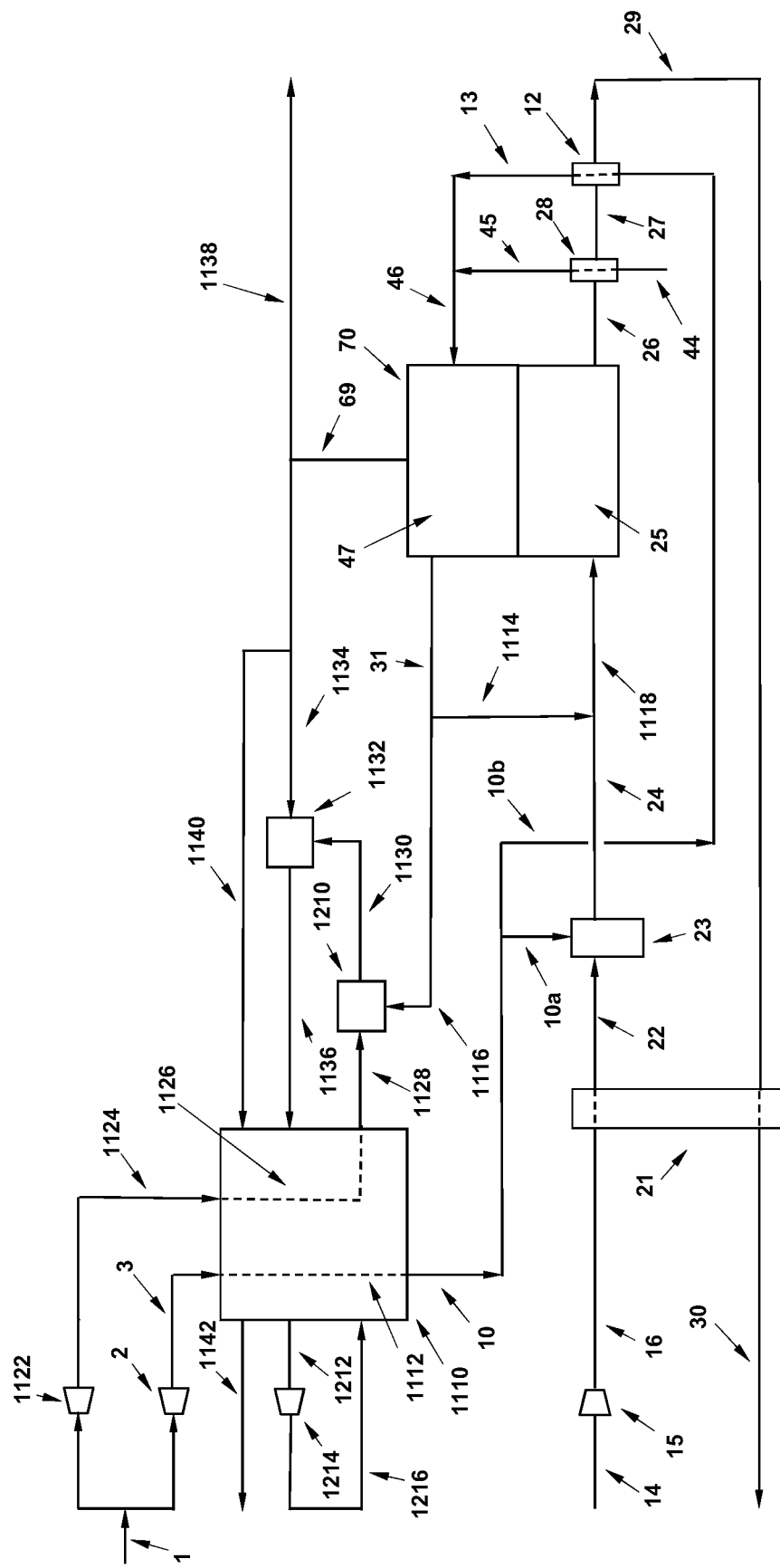
FIG. 12 is a variation of the process diagram in FIG. 11 where the process is operated under vacuum.

Referring now to FIG. 12, another process that produces methanol is shown. The process arrangement differs from FIG. 11 in that the TRM unit 1110 operates under negative pressure versus positive pressure as shown in FIG. 11. Natural gas supply stream 1128 is mixed with fuel cell cathode exhaust stream 1116 in mixing unit 1210. The mixed stream 1130 enters on-line electric unit 1132 where it is heated to a desired mixture temperature and output as heated stream 1136 before entering TRM unit 1110 as a reaction stream. The negative pressure is controlled by compressor and/or vacuum pump 1214 through stream 1212, which is then routed back to TRM unit 41 through stream 1216. This proposed method is an alternative mode of TRM unit operation at negative pressures versus positive operating pressures as shown in FIG. 11.

Those skilled in the art will recognize and appreciate the alternative feature of this method, where the reactants and energy produced by a fuel cell enables this process to produce methanol at near zero GHG emissions. Moreover, those skilled in the art will appreciate the efficiency of on-line electric heating versus the typical gas operated furnaces, although gas operated furnaces may also be used. The on-line electric heaters may also be an electric furnace. The ability to control pressure and temperature before and after mixing the reactants allows for operations optimization to maximize the process efficiency.

Figure 13:
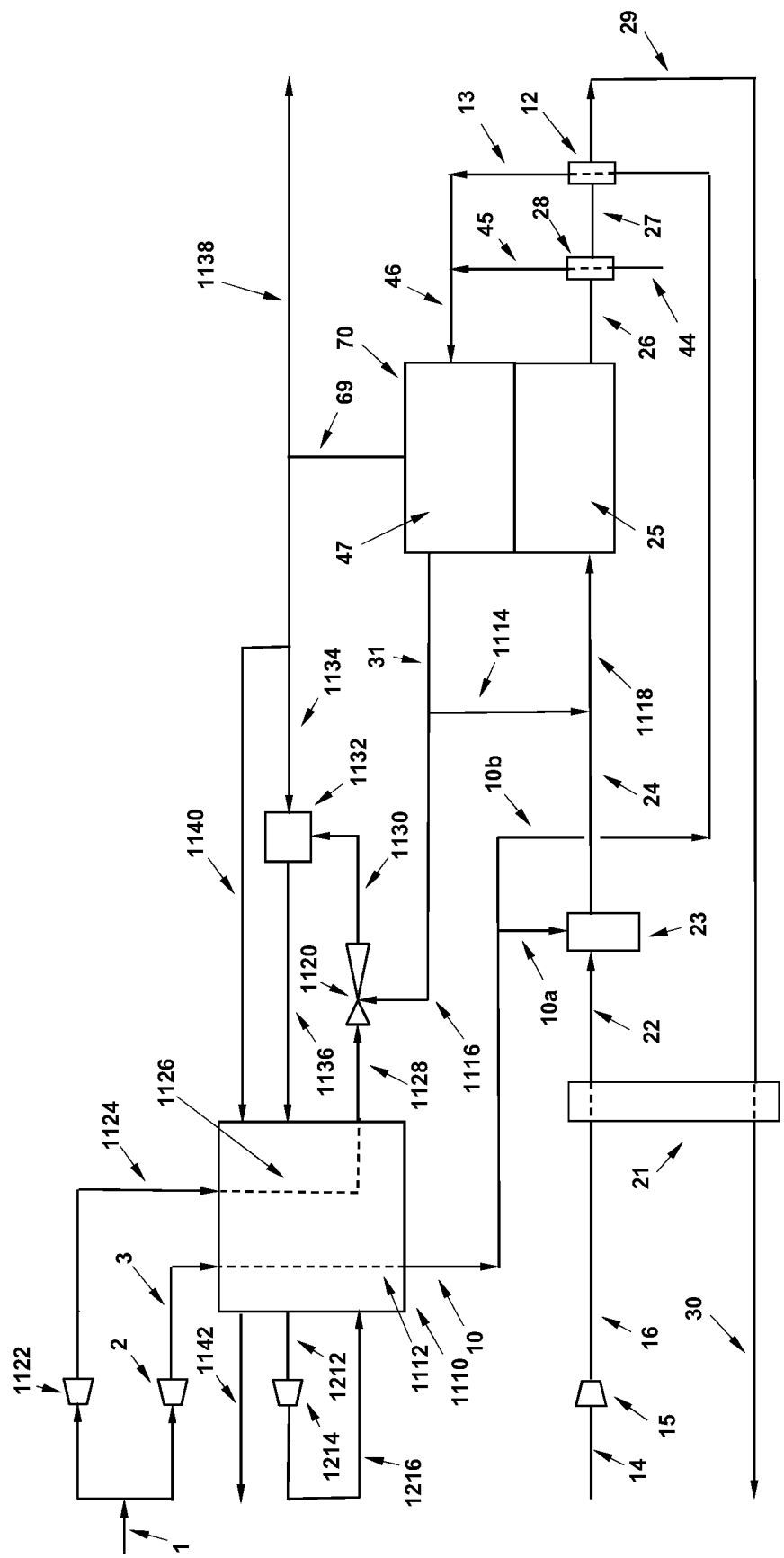
FIG. 13 is a variation of the process diagram in FIG. 11 and FIG. 12 where the process is operated under a balanced pressure.

Referring to FIG. 13, another process arrangement is depicted, which differs from FIG. 11 and FIG. 12 in that the TRM unit 1110 has a balanced operating pressure to meet optimum operating conditions in a catalytic or non-catalytic process. The positive pressure is supplied by jet pump 1120 which draws in the cathode exhaust stream 13 to form the TRM mixture stream and compressor and or vacuum pump 1214 provides the balance pressure of the process circuit from stream 1130 to stream 1212.

Figure 14:
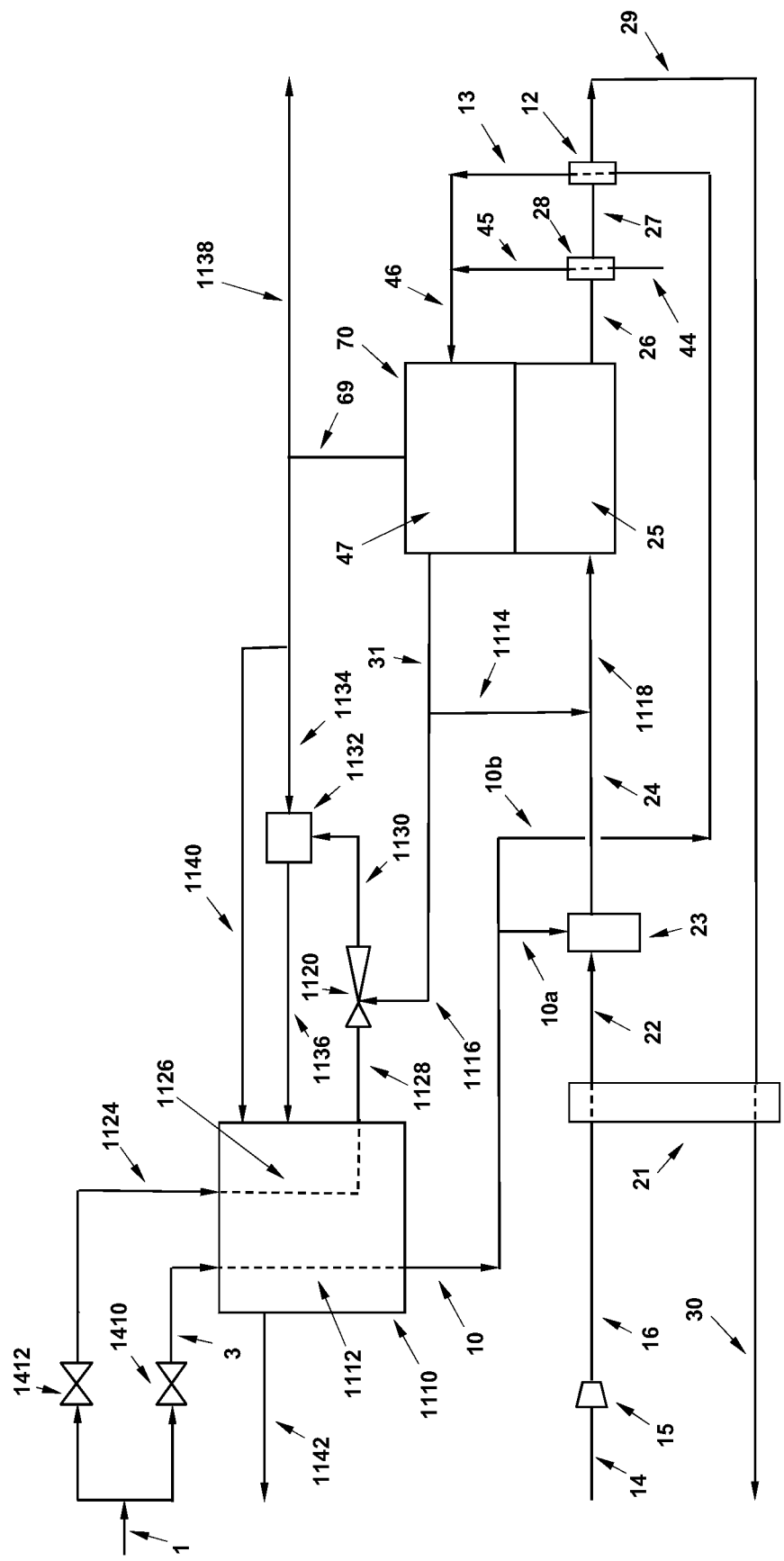
FIG. 14 is a variation of the process diagram in FIG. 11 where the process where natural gas supply pressure letdown is through JT valves versus gas expanders/generators.

Referring to FIG. 14, another process arrangement is depicted, which differs from FIG. 11 in that natural gas supply expanders/generators 2 and 1122 are replaced by JT valves 1410 and 1412, respectively, to control the natural gas pressure to the fuel cell and TRM unit 1110. In this mode of operation the cold temperatures generated in streams 3 and 1124 are not as cold, and hence less cooling from these streams will be available to TRM unit 1110. Moreover, there will not be power generated as in expander/generators 2 and 1122.

Figure 15:
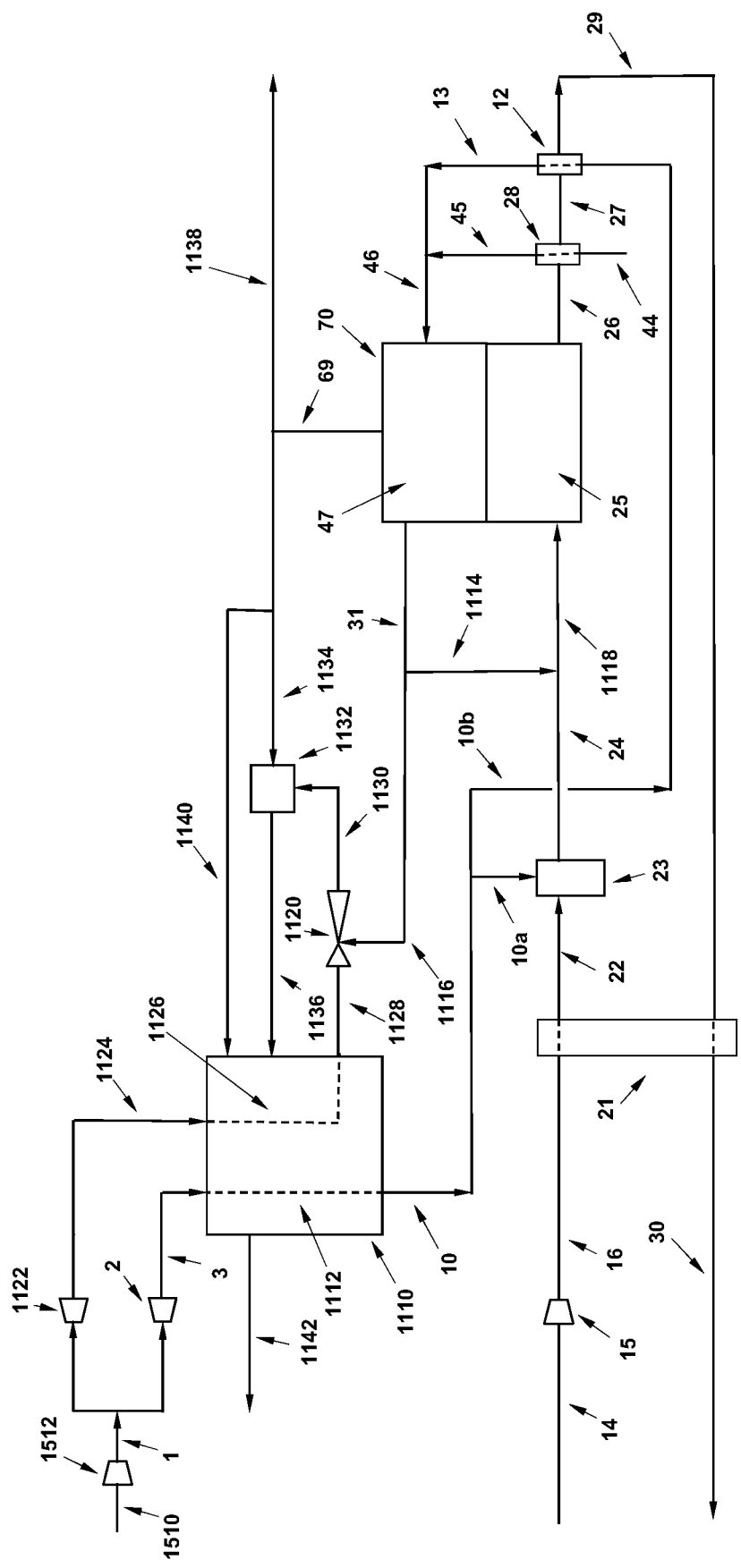
FIG. 15 is a variation of the process diagram in FIG. 11 where the process where natural gas supply pressure is further boosted before pressure letdown gas expanders/generators.

Referring to FIG. 15, another process arrangement is depicted, which differs from FIG. 11 in that the pressure in a natural gas supply stream 1510 is increased by compressor 1512 prior to the natural gas supply line 1 and prior to expanders/generators 2 and 1122. This allows another option to meet the pressure or cooling requirements of the TRM unit 1110.

Figure 16:
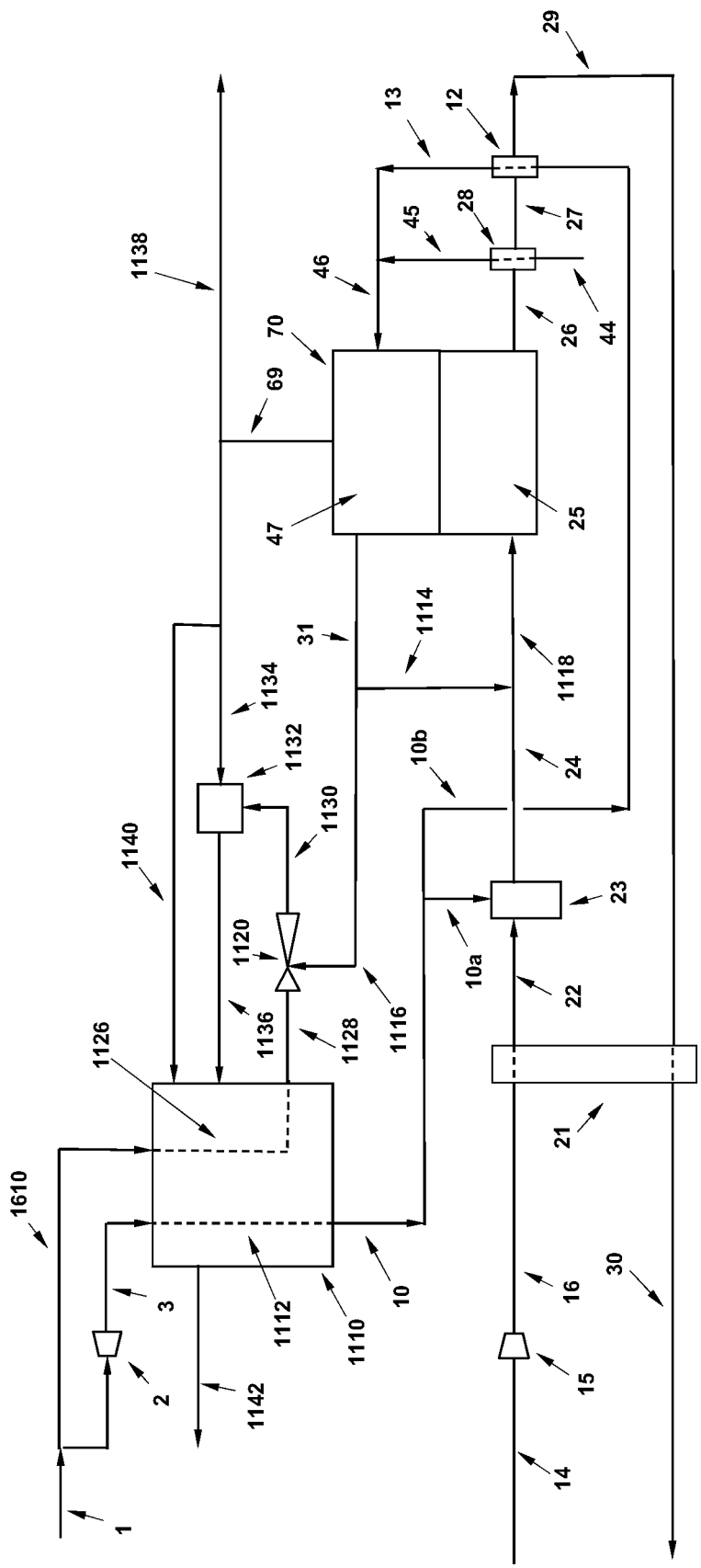
FIG. 16 is a variation of the process diagram in FIG. 15 where the process where natural gas supply to the TRM unit is at natural gas supply pressure.

Referring to FIG. 16, another process arrangement is depicted, which differs from FIG. 11 in that natural gas supply stream 1610 to the TRM unit provides for higher operating pressures if desired. In this process arrangement the TRM unit operating pressure is determined by the gas pressure supplied by stream 1610. If additional pressure is required in stream 1610 a booster compressor can be added to this stream.

Figure 17:
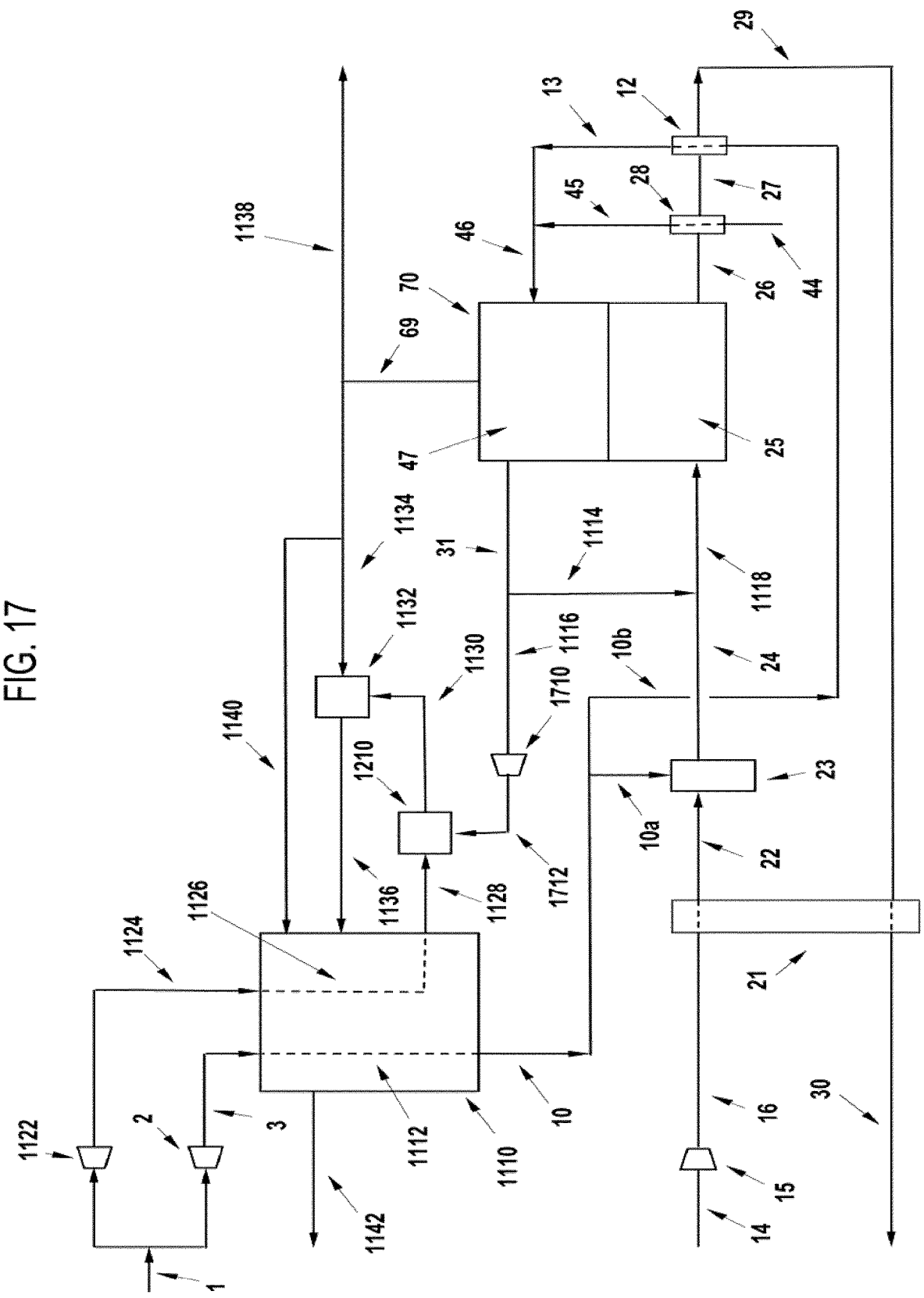
FIG. 17 is a variation of the process diagram in FIG. 12 where the cathode exhaust stream to the mixer is pressure boosted.

Referring to FIG. 17, another alternative is shown, in which the pressure of the anode exhaust stream 1116 is boosted by a compressor 1710, and the compressed anode exhaust stream 1712 is then mixed with natural gas stream 1128 in mixer 1210.

Fuel cells are presently in operation in sizes up to 59 MW and easily scalable to larger sizes. These power generation fuel cell sizes produce carbon dioxide, water and nitrogen streams as a by-product of power generation that permits the production of methanol at near zero GHG emissions using established and proven catalytic processes. The proposed process produces methanol by beneficially using highly concentrated, high quality streams of water and carbon dioxide that are flow controlled at optimum ratios and temperature controlled at optimum temperatures to maximize reactor efficiency. In addition, the thermal energy of the fuel cell exhaust streams is fully recovered to enhance the energy efficiency of the process due to its use as a preheater. Moreover, the use of produced electrical power to provide the thermal energy requirements of direct methane to methanol process through on-line electric heaters, electric furnaces and or electric heating elements to allow for the production of methanol at near zero GHG emissions. As can be appreciated the proposed method provides for various heat exchangers orientation to maximize heat recovery and efficiency of the fuel cell exhaust streams, recovered exhaust stream components and natural gas streams.

Those skilled in the art will recognize and appreciate the feature of the shown methods where the reactants and energy produced by a fuel cell enables the production of methanol from two inputs natural gas and atmospheric air at near zero GHG emissions. In particular, it will be apparent that this process is applicable to a wide range of fuel cell exhaust streams.

It will be understood that, while the process described herein teaches a single source for each of the components used in the reaction, that alternatives may involve other sources of reactants. For example, the exhaust components as described herein may be supplemented with carbon dioxide and water or other components from other sources. In addition, the natural gas may be provided separately from the fuel stream of the fuel cell. Other modifications may also be made in line with the teachings described above.

Those knowledgeable in the art will recognize and appreciate the features of the shown methods allow the reactants and energy produced by a fuel cell to enable various processes that produce petrochemical feedstock and products from two inputs into the fuel cell, i.e. natural gas and atmospheric air, at near zero GHG emissions. The methods described allow for one or more components of a fuel cell exhaust stream to be used to produce petrochemicals, and may allow for other outputs of the fuel cell to be used in the petrochemical production process, or to be diverted to other processes or for other purposes. This process may be adapted to any suitable fuel cell exhaust streams.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

The scope of the claims should not be limited by the preferred embodiments set forth in the examples, but should be given a broad purposive interpretation consistent with the description as a whole.

What is claimed is:

1. A method of producing petrochemicals using a hydrocarbon fuel cell, comprising the steps of:

operating the fuel cell to produce electricity, thermal energy, and an exhaust stream, the exhaust stream comprising at least a carbon-containing gas and water, the fuel cell receiving a fuel stream of natural gas and a stream of atmospheric air as inputs;

heating a reactant stream of natural gas using some or all of the electricity, some or all of the thermal energy, or a combination thereof to produce a heated reactant stream of natural gas; and combining at least a portion of the exhaust stream with the heated reactant stream of natural gas into a reactor input stream, and reacting the reactor input stream in a reactor to produce one or more petrochemical streams.

2. The method of claim 1, wherein the carbon-containing gas and the water are produced from an anode of the fuel cell.

3. The method of claim 1, wherein the exhaust stream further comprises a nitrogen-containing gas produced from a cathode of the fuel cell.

4. The method of claim 1, wherein at least a portion of the thermal energy is carried by the exhaust stream.

5. The method of claim 4, wherein the thermal energy is used to preheat the reactant stream of natural gas.

6. The method of claim 1, wherein the one or more petrochemical streams comprises one or more petrochemicals selected from a group consisting of: synthesis gas, methanol, ammonia, urea, polymers, prepolymers, hydrocarbon fuels, acetic acid, and glycol.

7. The method of claim 1, further comprising the step of separating the carbon-containing gas and the water into separate streams using heat exchangers and phase separators.

8. The method of claim 1, wherein the reactant stream of natural gas and the at least a portion of the exhaust stream is preconditioned in heat exchangers using the thermal energy produced by the fuel cell.

9. The method of claim 1, further comprising the step of powering at least one of material handling equipment and heating equipment of the reactor using electricity produced by the fuel cell.

10. The method of claim 1, wherein the reactant stream of natural gas comprises a slipstream of the fuel stream of natural gas.

11. The method of claim 1, wherein substantially all of the carbon in the carbon-containing gas is consumed in the reactor.

12. The method of claim 1, wherein the reactor conducts two or more reactions in parallel or in series.

13. The method of claim 1, wherein the at least a portion of the exhaust stream is mixed with the reactant stream of natural gas upstream of the reactor, the exhaust stream comprising a heated stream of carbon-containing gas and water vapor.

14. The method of claim 13, wherein the reactor is a tri-reform reactor (TRM) that produces methanol.

15. The method of claim 14, wherein the TRM is cooled by an expanded stream of natural gas, the reactant stream of natural gas being derived from the expanded stream of natural gas.

* * * * *